US010867698B2

(12) United States Patent
Putnam et al.

(10) Patent No.: US 10,867,698 B2
(45) Date of Patent: Dec. 15, 2020

(54) SYSTEMS AND METHODS FOR IMPROVED HEALTH CARE COHORT REPORTING

(71) Applicant: Intermountain Intellectual Asset Management, LLC, Salt Lake City, UT (US)

(72) Inventors: Ann Zofia Putnam, Salt Lake City, UT (US); Matthew Scott Peters, Salt Lake City, UT (US); Craig Gale, Salt Lake City, UT (US); Dallin Rogers, Salt Lake City, UT (US); Mark John Ott, Salt Lake City, UT (US)

(73) Assignee: Intermountain Intellectual Asset Management, LLC, Salt Lake City, UT (US)

( * ) Notice: Subject to any disclaimer, the term of this patent is extended or adjusted under 35 U.S.C. 154(b) by 1228 days.

(21) Appl. No.: 15/060,359

(22) Filed: Mar. 3, 2016

(65) Prior Publication Data

US 2016/0259916 A1 Sep. 8, 2016

Related U.S. Application Data

(60) Provisional application No. 62/129,480, filed on Mar. 6, 2015.

(51) Int. Cl.
*G16H 15/00* (2018.01)
*G06F 19/00* (2018.01)

(52) U.S. Cl.
CPC .......... *G16H 15/00* (2018.01); *G06F 19/328* (2013.01)

(58) Field of Classification Search
CPC ...... A61B 5/0022; G16H 50/70; G16H 15/00; G06F 19/328; G06F 19/325
USPC .......................................................... 705/2–3
See application file for complete search history.

(56) References Cited

U.S. PATENT DOCUMENTS

| | | | | |
|---|---|---|---|---|
| 2008/0086325 A1 | | 4/2008 | James | |
| 2014/0089003 A1* | | 3/2014 | Frey | G16H 10/60 705/3 |
| 2014/0164784 A1* | | 6/2014 | Sinderbrand | G06F 21/602 713/189 |
| 2014/0257047 A1* | | 9/2014 | Sillay | G16H 10/20 600/301 |

OTHER PUBLICATIONS

International Search Report and Written Opinion issued for PCT Application No. PCT/US2016/020854 dated May 23, 2016.

* cited by examiner

*Primary Examiner* — Joy Chng
(74) *Attorney, Agent, or Firm* — Stoel Rives LLP; Jordan B. Olsen

(57) ABSTRACT

A method for generating a report by a computing device is described. The method includes identifying a specific health care intervention. The method also includes creating a health care cohort for the specific health care intervention. The health care cohort includes a definition of a primary intervention. The method further includes generating a report based on the health care cohort.

20 Claims, 15 Drawing Sheets

1400
Perform a preliminary extraction from one or more databases based at least on a primary intervention code — 1402
Store a set of encounters in a health care prehort table — 1404
Generate a user interface control that provides a selection between at least two anatomical options or at least two health care interventions options — 1406
Present a health care encounter from the health care prehort table on a user interface, where the user interface includes the user interface control for the health care encounter — 1408
Proceed to next encounter in the health care prehort table — 1418
Optionally highlight one or more keywords in the clinical notes for the health care encounter — 1410
Receive a selected anatomical option or a health care intervention option — 1412
1414 Does the selected option qualify the encounter for inclusion in the health care cohort?
No: Optionally add the health care encounter to a health care exhort — 1416
Yes: Add the health care encounter to the health care cohort — 1420
1422 Encounter(s) remaining? Yes / No
Generate report(s) based on the health care cohort — 1424

SYSTEMS AND METHODS FOR IMPROVED HEALTH CARE COHORT REPORTING

RELATED APPLICATIONS

This application is related to and claims priority from U.S. Provisional Patent Application Ser. No. 62/129,480, filed Mar. 6, 2015 for "SYSTEMS AND METHODS FOR IMPROVED COMPARISON OF HEALTH CARE COSTS, UTILIZATION AND OUTCOMES," which is incorporated herein by reference.

TECHNICAL FIELD

The present disclosure relates generally to health-related systems and technologies. More specifically, the present disclosure relates to systems and methods for improved health care cohort reporting.

BACKGROUND

Computer and communication technologies continue to advance at a rapid pace. Indeed, computer and communication technologies are involved in many aspects of a user's day. Computers commonly used include everything from hand-held computing devices to large multi-processor computer systems. Computer technology is becoming increasingly important in the medical services environment. For example, computers may assist health care providers in treating patients. Also, computer systems may be used in the medical environment to assist clinicians and other health care providers.

Health care providers often find that utilization rates of health care supplies and equipment, costs, and medical outcomes as well as patient outcomes for certain health care interventions vary significantly and are difficult to predict. Current analytic products on the market may not provide the detailed accuracy necessary to generate true comparisons in the cost, utilization rates, and medical outcomes of health care interventions. Without accurate comparisons, it is difficult for health care providers to set or reach goals for financial savings or improved patient outcomes and to predict medical costs for patients. Therefore, improvements in systems and methods for generating detailed analytic reports in the medical services environment may be beneficial.

DETAILED DESCRIPTION

Figure 1:
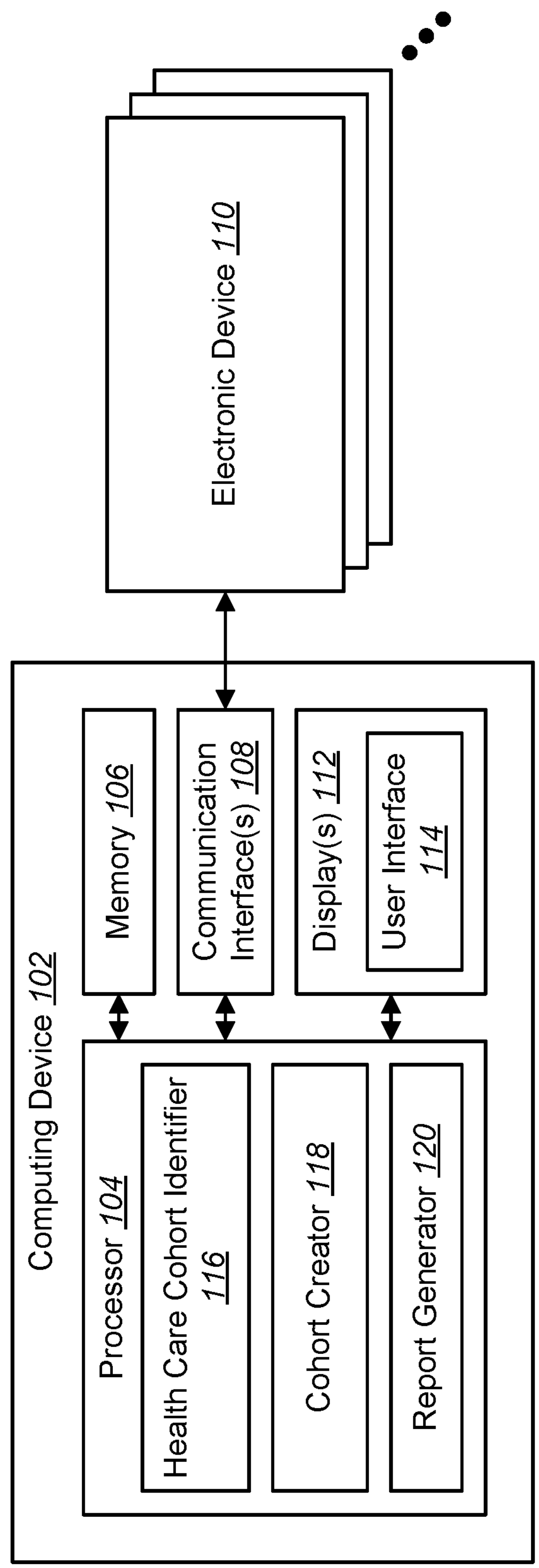
FIG. 1 is a block diagram illustrating one example of a computing device in which systems and methods for generating a report may be implemented.

A method for generating a report by a computing device is described. The method includes identifying a specific health care intervention. The method also includes creating a health care cohort for the specific health care intervention. The health care cohort includes a definition of a primary intervention. The method further includes generating a report based on the health care cohort. The method may include cleaning health care cohort data.

The health care cohort may include a list of associated acceptable secondary interventions. The health care cohort may include a list of exclusionary secondary interventions that if performed would exclude a corresponding encounter from the health care cohort.

The report may include a system-specific report. The system-specific report may include a hospital-specific or site-specific report. The report may include a health care provider-specific report. The report may include a list of cohorts organized relative to a cost variation per encounter compared to an average.

An apparatus for generating a report is also described. The apparatus includes a processor. The apparatus also includes memory in electronic communication with the processor. The apparatus further includes instructions stored in the memory. The instructions are executable to identify a specific health care intervention. The instructions are also executable to create a health care cohort for the specific health care intervention. The health care cohort includes a definition of a primary intervention. The instructions are further executable to generate a report based on the health care cohort.

A method for refining a health care prehort by a computing device is also described. The method includes performing a preliminary extraction from one or more databases based at least on a primary intervention code. The method also includes storing a set of encounters in a health care prehort table. The method further includes generating a user interface control that provides a selection between at least two anatomical options or at least two health care intervention options. The method additionally includes, for each encounter in the health care prehort table, presenting an encounter from the health care prehort table on a user interface. The user interface includes the user interface control for the encounter. The method also includes, for each encounter in the health care prehort table, receiving a selected anatomical option or a health care intervention option. The method further includes, for each encounter in the health care prehort table, adding the encounter to a health care cohort if the selected anatomical option or health care intervention option qualifies the encounter for inclusion in the health care cohort. The method additionally includes generating one or more reports based on the health care cohort. The method may include highlighting one or more keywords in clinical notes for the encounter.

An apparatus for refining a health care prehort is also described. The apparatus includes a processor. The apparatus also includes memory in electronic communication with the processor. The apparatus further includes instructions stored in the memory. The instructions are executable to perform a preliminary extraction from one or more databases based at least on a primary intervention code. The instructions are also executable to store a set of encounters in a health care prehort table. The instructions are further executable to generate a user interface control that provides a selection between at least two anatomical options or at least two health care intervention options. The instructions are additionally executable to, for each encounter in the health care prehort table, present an encounter from the health care prehort table on a user interface. The user interface includes the user interface control for the encounter. The instructions are also executable to, for each encounter in the health care prehort table, receive a selected anatomical option or a health care intervention option. The instructions are further executable to, for each encounter in the health care prehort table, add the encounter to a health care cohort if the selected anatomical option or health care intervention option qualifies the encounter for inclusion in the health care cohort. The instructions are additionally executable to generate one or more reports based on the health care cohort.

Health care providers often find that costs, utilization rates, and outcomes for certain health care interventions vary significantly and are difficult to predict. Some products provide detailed utilization analytics for health care providers, but those products' health care intervention comparisons include but are not limited to medical billing procedure codes or diagnostic codes, such as International Classification of Diseases (ICD) (e.g., ICD-9, ICD-10, other ICD codes, etc.) or Current Procedural Terminology (CPT) codes, as well as other widely recognized coding terminologies identified in the national health care registries. These comparisons are generally termed cost-per-case reports. By generating cost-per-case reports and outcome comparisons using general billing codes organized under one or more codes, the findings may not account for variability in individual health care interventions, such as, for example, whether the intervention was a primary or secondary intervention and differences in potentially relevant demographic information. Accordingly, current analytic products on the market may not provide the detailed accuracy necessary to generate true comparisons in the cost, utilization rates, and outcomes of health care interventions. Without accurate comparisons of health care interventions, it is difficult for health care providers to set or reach goals for financial savings or improved patient outcomes and to predict medical costs for patients. Therefore, improvements in systems and methods for generating detailed analytic reports in the medical services environment may be beneficial.

Systems and methods for improved comparison of health care intervention costs, utilization rates, and outcomes in the health care environment are described. The systems and methods include identifying health care interventions, which represents a key improvement over existing systems and methods for health care intervention cost-per-case reports. A health care intervention may be (e.g., may represent) an action taken by a health care provider in behalf of a patient and/or a record of one or more actions taken by a health care provider in behalf of a patient. Examples of health care interventions may include primary interventions, acceptable secondary interventions and/or secondary interventions that if performed would exclude a particular encounter from being included in the health care cohort. For example, a health care cohort may be a clinically defined group of patient encounters that may be identified using one or more parameters (e.g., existing data codes, newly created data codes, data from one or more hospital information systems (HIS), etc.). A health care cohort may be defined in terms of one or more interventions. For instance, a health care cohort may include encounters that may involve a primary intervention and/or a defined list of associated acceptable secondary interventions, but that may not involve a defined list of secondary interventions that if performed would exclude a particular encounter from being included in the health care cohort. An encounter may represent (e.g., may be a record of) an interaction between a patient and a health care provider. A health care provider may request the identification of one or more health care cohorts if he or she is not satisfied with existing cost-per-case data that is currently limited to analysis of specific billing procedure or diagnostic codes, including but not limited to ICD or CPT codes, or other coding terminology from the national health care registries. In this improved approach, the queries for health care cohorts may be created using existing and widely recognized health care terminologies, including but not limited to ICD procedure codes and CPT codes, as well as multiple other criteria to ensure true comparison of similar health care interventions. The method for identifying a health care cohort will be further described below.

The systems and methods also include generating detailed analytic reports based on the selected health care cohort. The reports may be used to review and prepare data to share with health care providers and health care administrators. The report may display a site-specific (e.g., hospital-specific, clinic-specific, surgical suite-specific, etc.) list of health care cohorts organized relative to the variation of cost compared to the system average. The report may also show how a specific health care cohort's system average compares by region average, by one or more individual facilities, and/or by physician. The report allows customization of health care cohorts related to date range, age, severity of illness, gender, and insurance type. The type of cost that is displayed may also be customized.

Comparative data in the report may include variables specific to medical services, such as operating room time, staffing, and supplies used. The report may also include utilization data for length of stay, nursing/floor costs, lab costs, pharmacy costs, post-anesthesia care unit (PACU) time, average PACU charge, therapy costs, imaging costs, and other costs. Users may view a trend graph that depicts the selected health care providers' trend for the previous year for time, volume of cases, supply costs, supply charges, total costs, and the reimbursement a hospital or network received for the selected health care cohort.

The systems and methods disclosed herein may allow for improved comparison of health care intervention costs and outcomes. For example, these systems and methods may allow a medical provider to more accurately understand how costs and outcomes for a specific health care intervention compares to the system average, region average, and how it compares for individual facilities. Further, this method for identifying a health care cohort and generating detailed comparison reports may be beneficial for health care providers seeking to set or reach budget and outcome goals and to more accurately predict costs and outcomes for patients.

The systems and methods disclosed herein may fulfill a need in the medical industry. For example, existing approaches to quantify medical costs may not provide specific health care intervention implementation comparisons. For example, existing approaches may not offer specific data that illustrate specific routes to costs savings. However, the systems and methods disclosed herein may offer comparisons of encounters where homogenous and specific health care interventions were performed. This provides specific routes to cost savings, in that cost-saving execution of specific health care interventions may be identified. For example, differences in supply usage between performances of a specific health care intervention may illustrate less costly supplies and/or quantities needed to perform the specific health care intervention. The systems and methods disclosed herein may facilitate cost savings in the medical industry.

Various configurations are now described with reference to the figures, where like reference numbers may indicate functionally similar elements. The systems and methods as generally described and illustrated in the figures herein could be arranged and designed in a wide variety of different configurations. Thus, the following more detailed description of several configurations, as represented in the figures, is not intended to limit scope, as claimed, but is merely representative of the systems and methods.

FIG. 1 is a block diagram illustrating one example of a computing device 102 in which systems and methods for generating a report may be implemented. In some configurations, the report may compare health care intervention costs, utilization rates, and/or outcomes. Examples of the computing device 102 include computers (e.g., desktop computers, laptop computers, servers, supercomputers, etc.), smart phones, tablet devices, health care equipment, etc. The computing device 102 may include one or more components or elements. One or more of the components or elements may be implemented in hardware (e.g., circuitry) or a combination of hardware and software (e.g., a processor with instructions).

In some configurations, the computing device 102 may perform one or more of the functions, procedures, methods, steps, etc., described in connection with one or more of FIGS. 1-14. Additionally or alternatively, the computing device 102 may include one or more of the structures described in connection with one or more of FIGS. 1-14.

In some configurations, the computing device 102 may include one or more processors 104, memory 106 (e.g., one or more memory circuits, random access memory (RAM) circuits, RAM chips, etc.), one or more displays 112 and/or one or more communication interfaces 108. The processor 104 may be coupled to (e.g., in electronic communication with) the memory 106, display 112 and/or communication interface 108. It should be noted that one or more of the elements of the computing device 102 described in connection with FIG. 1 (e.g., communication interface(s) 108, display(s) 112, etc.) may be optional and/or may not be included (e.g., implemented) in the computing device 102 in some configurations.

The processor 104 may be a general-purpose single- or multi-chip microprocessor, a special-purpose microprocessor (e.g., a digital signal processor (DSP)), a microcontroller, a programmable gate array, etc. The processor 104 may be referred to as a central processing unit (CPU). Although just a single processor 104 is shown in the computing device 102, in an alternative configuration, a combination of processors could be used. The processor 104 may be configured to implement one or more of the methods disclosed herein. The processor 104 may include and/or implement a health care cohort identifier 116, a cohort creator 118, and/or a report generator 120 in some configurations.

The memory 106 may be any electronic component capable of storing electronic information. For example, the memory 106 may be implemented as random access memory (RAM), read-only memory (ROM), magnetic disk storage media, optical storage media, flash memory devices in RAM, on-board memory included with the processor, EPROM memory, EEPROM memory, registers, and so forth, including combinations thereof.

The memory 106 may store instructions and/or data. The processor 104 may access (e.g., read from and/or write to) the memory 106. The instructions may be executable by the processor 104 to implement one or more of the methods described herein. Executing the instructions may involve the use of the data that is stored in the memory 106. When the processor 104 executes the instructions, various portions of the instructions may be loaded onto the processor 104 and/or various pieces of data may be loaded onto the processor 104. Examples of instructions and/or data that may be stored by the memory 106 may include image data, health care cohort identifier 116 instructions, cohort creator 118 instructions and/or report generator 120 instructions, etc.

The communication interface(s) 108 may enable the computing device 102 to communicate with one or more other electronic devices 110. For example, the communication interface(s) 108 may provide one or more interfaces for wired and/or wireless communications. In some configurations, the communication interface(s) 108 may be coupled to one or more antennas for transmitting and/or receiving radio frequency (RF) signals. Additionally or alternatively, the communication interface 108 may enable one or more kinds of wireline (e.g., Universal Serial Bus (USB), Ethernet, etc.) communication.

In some configurations, multiple communication interfaces 108 may be implemented and/or utilized. For example, one communication interface 108 may be an Ethernet interface, another communication interface 108 may be a universal serial bus (USB) interface, another communication interface 108 may be a wireless local area network (WLAN) interface (e.g., Institute of Electrical and Electronics Engineers (IEEE) 802.11 interface) and yet another communication interface 108 may be a cellular (e.g., 3G, Long Term Evolution (LTE), CDMA, etc.) interface.

The computing device 102 and/or one or more electronic devices 110 may store medical information. Medical information may include diagnosis information, treatment (e.g., treatment procedure) information, billing information, medical records and/or inventory information, etc. For instance, medical information may be stored in one or more databases (e.g., in an Enterprise Data Warehouse (EDW)). In some configurations, the medical information may be stored in a repository (e.g., EDW) that integrates multiple disparate sources (e.g., medical records database, billing database, imaging database, hospital information system (HIS), picture archiving and communication system (PACS), radiology information system (RIS), etc.). In some configurations, the communication interface 108 may receive information (e.g., medical information, health care information, medical records, billing records, etc.) from one or more electronic devices 110 (e.g., a remote server, another computing device, networked storage, etc.) and/or send information (e.g., medical information, health care information, cohort information, report information, etc.) to one or more electronic devices 110. Additionally or alternatively, the computing device 102 may access medical information that is stored on the computing device 102.

The display(s) 112 may be integrated into the computing device 102 and/or may be coupled to the computing device 102. Examples of the display(s) 112 include liquid crystal display (LCD) screens, light emitting display (LED) screens, organic light emitting display (OLED) screens, plasma screens, cathode ray tube (CRT) screens, etc. In some implementations, the computing device 102 may be a smartphone with an integrated display. In another example, the computing device 102 may be coupled to one or more remote displays 112 and/or to one or more remote devices that include one or more displays 112.

In some configurations, the computing device 102 may present a user interface 114 on the display 112. For example, the user interface 114 may enable a user to interact with the computing device 102. In some configurations, the user interface 114 may enable a user to input information. For example, the user interface 114 may receive text input (from a keyboard, for instance), a mouse click, a touch, a gesture and/or some other input.

The processor 104 may include and/or implement a health care cohort identifier 116. The health care cohort identifier 116 may identify one or more specific health care interventions. A specific health care cohort may be defined in accordance with a health care intervention that is carried out in a specific way. For example, a specific health care cohort may be defined by a health care intervention that follows one or more specific steps (e.g., techniques) on a specific anatomy and/or that is distinguished from other health care interventions in the anatomy and/or execution of one or more steps (e.g., techniques). A specific health care cohort may be more specific than a general health care intervention (e.g., a category of health care intervention). For example, a "spinal fusion" may be a general health care intervention, while a 1 level spinal fusion, 2 level spinal fusion, 3 level spinal fusion, etc., may be examples of specific health care interventions. In another example, a hysterectomy may be a general health care intervention, although there are multiple ways to carry out a hysterectomy. Examples of hysterectomies that may define specific health care cohorts may include abdominal hysterectomy, a laparoscopic hysterectomy, a robotic laparoscopic hysterectomy (e.g., laparoscopic hysterectomy using the Da Vinci surgical system, etc.), etc.

A specific health care cohort may be mutually exclusive from another specific health care cohort (which may fall under the same general health care intervention). For example, a specific health care intervention may include one or more elements (e.g., techniques, tools, steps, anatomy, etc.) that are different from (e.g., different from, not included in, etc.) another specific health care intervention. For instance, a laparoscopic hysterectomy may utilize a laparoscope, while an abdominal hysterectomy may not. In another example, a 2 level spinal fusion may involve anatomy (e.g., another level of the spine) that is not involved in a 1 level spinal fusion. A specific health care cohort may be more specific than standard medical codes. For example, a standard medical code (e.g., CPT code) may only have one code for a "spinal fusion," even though there may be several kinds of spinal fusions, which may be based on the anatomy involved (e.g., number of spinal levels, location of spinal levels, etc.) and/or procedures utilized to perform the spinal fusion. It should be noted that for some health care cohorts, there may be little procedural and/or anatomical variation between interventions. For example, some health care cohorts may include health care interventions performed only one way and on the same anatomy in all cases or encounters. Accordingly, a specific health care cohort may include a health care intervention that is only performed one way and on the same anatomy in all cases or encounters.

In some configurations, the health care cohort identifier 116 may identify one or more specific health care interventions based on received input. For example, the health care cohort identifier 116 may receive an input (e.g., text input from a keyboard, a mouse click, etc.) that indicates a specific health care intervention. In some approaches, the received input may include the name of a specific health care intervention. For example, a health care provider (e.g., surgeon), data manager and/or other user may input an identifier (e.g., name) of a specific health care intervention.

In some configurations, the health care cohort identifier 116 may determine a primary intervention code that covers the specific health care intervention. For example, the health care cohort identifier 116 may receive an input that indicates the primary intervention code (e.g., ICD code, CPT code, billing code, etc.). A primary intervention code may indicate a health care intervention group. A health care intervention group may be a group of specific primary intervention codes. For example, a primary intervention code that generally indicates "spinal fusion" may cover many types of spinal fusions (e.g., 2 level spinal fusion, 3 level spinal fusion, etc.). In some approaches, the health care cohort identifier 116 may automatically determine the primary intervention code that covers the specific health care intervention. For example, the health care cohort identifier 116 may search for and/or select one or more primary intervention codes that generally match a specific health care health care intervention.

Additionally or alternatively, the health care cohort identifier 116 may perform cost and/or encounter analysis. For example, the health care cohort identifier 116 may perform analysis on one or more health care intervention groups. A health care intervention group may be a group of health care interventions that may be indicated based on one or more parameters. For example, one or more primary intervention codes (e.g., standard medical codes, ICD codes, CPT codes, etc.) may indicate a health care intervention group. In some approaches, the health care cohort identifier 116 may request and/or retrieve medical information (e.g., clinical detail, costs, billing information, etc.) pertaining to the health care intervention group(s) (associated with one or more standard medical codes, for example). The health care cohort identifier 116 may analyze the medical information to determine one or more measures. For example, the health care cohort identifier 116 may determine one or more statistical measures (e.g., average, standard deviation, variance, coefficient of variation, etc.) for encounters in each health care intervention group. For instance, the health care cohort identifier 116 may determine a proportion of encounters with costs that are more than one standard deviation from the average, may determine a total dollar amount of encounters with above average cost, may determine the coefficient of variation in the cost of the encounters, and/or may determine the contribution to margin. For example, the coefficient of variation and/or contribution to margin may be metrics that may help identify whether a physician and/or hospital is performing better or worse than their counterparts and may represent an opportunity for a deeper dive into the data. The coefficient of variation may represent the degree of dispersion from the mean. For example, assume hospital A did five appendectomy surgeries. Their total costs were 1100, 1000, 1050, 975 and 900 with a mean of 1005. It should be noted that costs may be expressed in currency value (e.g., dollars) or in other units. Hospital B did five appendectomy surgeries and their total costs were 805, 1005, 1205, 705, 1305 (mean of 1005). In this situation both hospitals have the same mean cost but hospital B would have a greater coefficient of variation. Contribution to margin may be how much money the hospital profits off a particular surgery. If hospital A has a greater contribution to margin for appendectomy surgeries than hospital B, it may be beneficial to determine why hospital A has a greater contribution to margin.

Based on the analysis, the health care cohort identifier 116 may identify one or more health care interventions. For example, the health care cohort identifier 116 may indicate one or more encounters that exhibit opportunities for cost savings and/or increased margin. For instance, the health care cohort identifier 116 may indicate one or more encounters that have exceeded a threshold proportion of costs more than one standard deviation from the average of the health care cohort. Additionally or alternatively, the health care cohort identifier 116 may indicate one or more encounters based on a total dollar amount of cases or encounters with costs above a standard deviation from average cost (where the total dollar amount is above a threshold, for example). Additionally or alternatively, the health care cohort identifier 116 may indicate one or more encounters that have a coefficient of variation above a threshold. Additionally or alternatively, the health care cohort identifier 116 may indicate one or more encounters that have a contribution to margin below a threshold. For one or more of the indicated encounters, the health care cohort identifier 116 may (automatically) generate a name for a specific health care intervention. Additionally or alternatively, the health care cohort identifier 116 may generate a message (for transmission or display, for example) requesting a name for a specific health care cohort identifier and/or suggest creating one or more cohorts for each of the indicated health care intervention groups.

The processor 104 may include and/or implement a cohort creator 118. The cohort creator 118 may create one or more health care cohorts for the one or more specific health care interventions. A health care cohort may include a definition of a primary intervention (e.g., health care intervention, surgery, operation, treatment, etc.). A primary intervention definition may include one or more parameters. For example, a primary intervention definition may include the specific health care cohort identifier (e.g., name), may include one or more primary intervention codes and/or may include one or more other parameters (e.g., diagnosis code (s), billing group(s), associated provider specialty(ies), patient demographics, etc.). More specific examples are given in connection with FIG. 6. A health care cohort may also include a list of one or more associated acceptable secondary interventions (if any exist or are identified, for example). An acceptable secondary intervention may be a health care intervention that may be performed with the primary intervention. For example, an acceptable secondary intervention may be performed in addition to the primary intervention while still being consistent with the health care cohort. For instance, if an acceptable secondary intervention accompanies a primary intervention in an encounter, then the encounter may still qualify for (e.g., may be included within) the respective health care cohort. One example of a primary intervention may be a spinal fusion with a laminectomy as an example of an acceptable secondary intervention. Additionally or alternatively, the health care cohort may include a list of one or more exclusionary secondary interventions (if any exist or are identified, for example). An exclusionary secondary intervention may not be performed in addition to the primary intervention while still being consistent with the health care cohort. For example, if an exclusionary secondary intervention is performed in an encounter, then that particular encounter would be excluded from the health care cohort. For example, in a laparoscopic appendectomy cohort, the primary intervention may be the removal of the appendix, but if a secondary intervention of gallbladder removal is also done, this encounter may no longer meet the definition of the laparoscopic appendectomy cohort and will not be assigned to this cohort. In some approaches, this excluded encounter may be assigned to an exclusionary health care cohort (e.g., health care exhort). In some configurations, creating a health care cohort may include determining the primary intervention definition, determining any acceptable secondary intervention(s), and/or determining any exclusionary secondary intervention(s).

The cohort creator 118 may create one or more health care cohorts. For example, the cohort creator 118 may determine one or more encounters that are consistent with the health care cohort (for inclusion in the health care cohort). For instance, the cohort creator 118 may determine one or more encounters where the primary intervention was performed. Optionally, the cohort creator 118 may determine one or more encounters where the primary intervention was performed, where (optionally) one or more acceptable secondary interventions were performed, and/or where no exclusionary secondary intervention was performed. The one or more determined encounters may be included in the health care cohort (e.g., listed in a health care cohort table).

In some configurations, creating a health care cohort may include extracting data. For example, the cohort creator 118 may extract data (e.g., billing information, cost information, clinical notes (e.g., operation notes, health care provider notes, health care provider dictation, etc.), diagnosis information (e.g., diagnosis description, diagnosis date(s), ICD code(s), etc.), treatment information (e.g., treatment description, treatment date(s), CPT code(s), etc.), imaging information (e.g., x-ray(s), magnetic resonance imaging (MRI) data, photograph data, etc.), etc.). The data may be extracted from one or more databases (e.g., a data warehouse, EDW, etc.) stored on the computing device 102 and/or on one or more of the electronic devices 110. For example, the cohort creator 118 may extract the data by searching the one or more databases for cases or encounters with one or more criteria (e.g., ICD code(s), CPT code(s), keyword(s) in health care provider notes, date range(s), patient information, etc.). For example, the cohort creator 118 may search the database(s) for cases or encounters that have a primary intervention code (e.g., CPT code) associated with a health care intervention group.

In some configurations, extracting the data may include performing a preliminary extraction (e.g., pull) from one or more databases (e.g. EDW). For example, the cohort creator 118 may utilize the primary intervention code to extract cases or encounters with the primary intervention code. In some configurations, extracting the data may include determining one or more encounters for a preliminary cohort (e.g., health care "prehort"). In some configurations, the cohort creator 118 may store the health care prehort encounters in a health care prehort table in one or more databases (e.g., in an EDW). A health care prehort may include one or more encounters (e.g., a health care intervention group) that may meet one or more cohort criteria (e.g., primary intervention code), but where additional information may be utilized to make a determination whether the encounter(s) qualify for inclusion in the health care cohort.

For example, one or more cases or encounters with a primary intervention code (e.g., medical code, ICD code, CPT code, etc.) indicating a spinal fusion may be extracted into a health care prehort (e.g., a health care prehort table). In some configurations, the primary intervention code may not be specific enough to qualify a case or encounter for the corresponding cohort. For example, a health care cohort may include only encounters where a 2 level spinal fusion was performed, while the primary intervention code only indicates a spinal fusion in general.

In some approaches, the cohort creator 118 may arrange the health care prehort encounters for review. For example, the cohort creator 118 may highlight keywords (e.g., "level," "L1," "L2," "L3," "S1," "S2," etc.) in the clinical notes (e.g., operation notes) and present the clinical notes on the user interface 114. The cohort creator 118 may also generate and present a selection control on the user interface 114 (with the clinical notes, for example) for receiving input regarding whether the current encounter is a 2 level spinal fusion or not. The user interface 114 may receive a selection, which the cohort creator 118 may utilize to include the encounter in the health care cohort or exclude the encounter from the health care cohort. In some configurations, the cohort creator 118 may present a series of encounters on the user interface 114, which may allow for efficient categorization of the encounters for the health care cohort. For example, this may obviate the need for a health care provider to individually access the clinical notes for a set of encounters to determine whether an encounter should be included or not.

The cohort creator 118 may determine one or more characteristics of the health care prehort (e.g., frequency of encounters with primary intervention code, secondary interventions completed with the primary intervention and/or frequency of secondary interventions, etc.). For example, the cohort creator 118 may identify a frequency of encounters with a primary intervention code. For instance, the cohort creator 118 may determine how often (e.g., average frequency of) encounters with the primary intervention code arise. In some approaches, this may be accomplished by determining a number of cases or encounters with the primary intervention code over a period of time. The cohort creator 118 may determine (e.g., identify) one or more secondary interventions that may be completed with the primary intervention. For example, the cohort creator 118 may produce a list of secondary interventions that are completed with the primary intervention. In some approaches, the cohort creator 118 may also determine a frequency of secondary interventions. For example, this may be accomplished by determining a number of cases or encounters with the secondary intervention (e.g., medical code) over a period of time.

In some approaches, the cohort creator 118 may determine one or more exclusionary secondary interventions. For example, the cohort creator 118 may determine a list of one or more exclusionary secondary interventions for a health care cohort. In some configurations, the cohort creator 118 may determine the one or more exclusionary secondary interventions automatically. For example, the cohort creator 118 may determine one or more encounters that are excluded from the health care cohort. In some instances, the encounter (s) may be excluded based on one or more factors. For example, one or more encounters (which may have the same primary intervention code, for instance) may be excluded from the health care cohort based on a received selection (e.g., the encounter is not a 2 level spine fusion as described in the example above) and/or based on one or more parameters (e.g., patient demographics, provider specialty, hospital descriptor, clinical notes, etc.) in the primary intervention definition. The cohort creator 118 may determine one or more exclusionary secondary interventions in one or more encounters excluded from the health care cohort, where the one or more exclusionary secondary interventions are not found in any of the interventions included in the health care cohort.

In some configurations, the cohort creator 118 may present the health care cohort (e.g., prehort) for review. For example, the cohort creator 118 may present and/or send cohort information (e.g., primary intervention information, acceptable secondary intervention information, exclusionary secondary intervention information and/or one or more health care cohort encounters, etc.). For instance, the cohort creator 118 may present the health care cohort information on the display 112 (e.g., user interface 114). The cohort creator 118 may receive one or more change inputs. The change inputs may indicate one or more changes to the health care cohort information. For example, the change input(s) may specify adding one or more parameters (e.g., codes) to one or more of the primary intervention information, acceptable secondary intervention information and/or exclusionary secondary intervention information, etc. Additionally or alternatively, the change input(s) may specify removing one or more parameters to one or more of the primary intervention information, acceptable secondary intervention information and/or exclusionary secondary intervention information, etc. Additionally or alternatively, the change input(s) may specify adding one or more encounters. Additionally or alternatively, the change input(s) may specify removing one or more encounters. Presenting the health care cohort may allow a user (e.g., health care provider, physician, surgeon, nurse, etc.) an opportunity to change (e.g., add parameter(s) to, remove parameter(s) from, etc.) the health care cohort (e.g., prehort) such that the health care cohort accurately reflects the specific health care intervention.

In a situation where no change inputs are received (and/or if a health care cohort is approved), the cohort creator 118 may organize the health care cohort. In some configurations, for instance, the cohort creator 118 may organize the health care cohort. For example, the cohort creator 118 may organize the parameters that define the health care cohort. For instance, the cohort creator 118 may organize the definition of the primary intervention of the health care cohort. Organizing the definition of the primary intervention of the health care cohort may include identifying (e.g., associating, storing, etc.) one or more parameters for the primary intervention (e.g., the specific health care intervention). For example, the cohort creator 118 may identify (e.g., associate, store, etc.) one or more intervention codes (e.g., ICD codes, CPT codes), one or more diagnosis codes (e.g., ICD codes), one or more billing codes, one or more item types, one or more billing groups (e.g., All Patient Refined Diagnosis Related Groups (APRDRGs), Medicare Severity Diagnosis Related Groups (MSDRGs), etc.), one or more registries (e.g., Society of Thoracic Surgery (STS) database, etc.), illness severity, provider specialty, health care information system intervention code, trauma level, number of encounters, patient status, patient demographic (e.g., age, gender, etc.), clinical notes and/or other parameter(s), etc., for the primary intervention of a health care cohort. Additionally or alternatively, organizing the health care cohort may include identifying (e.g., associating, storing, etc.) one or more parameters for the acceptable secondary intervention(s). For example, the cohort creator 118 may identify (e.g., associate, store, etc.) one or more intervention codes (e.g., ICD codes, CPT codes), one or more diagnosis codes (e.g., ICD codes), one or more billing codes, one or more item types, one or more billing groups (e.g., APRDRGs, MSDRGs, etc.), one or more registries (e.g., STS database, etc.), illness severity, provider specialty, health care information system intervention code, trauma level, number of encounters, patient status, patient demographic (e.g., age, gender, etc.), clinical notes and/or other parameter(s), etc., for the acceptable secondary intervention(s) of a health care cohort. Additionally or alternatively, organizing the health care cohort may include identifying (e.g., associating, storing, etc.) one or more parameters for the exclusionary secondary intervention(s). For example, the cohort creator 118 may identify (e.g., associate, store, etc.) one or more intervention codes (e.g., ICD codes, CPT codes), one or more diagnosis codes (e.g., ICD codes), one or more billing codes, one or more item types, one or more billing groups (e.g., APRDRGs, MSDRGs, etc.), one or more registries (e.g., STS database, etc.), illness severity, provider specialty, health care information system intervention code, trauma level, number of cases or encounters, patient status, patient demographic (e.g., age, gender, etc.), clinical notes and/or other parameter(s), etc., for the exclusionary secondary intervention(s) of a health care cohort.

Upon organizing the health care cohort, the computing device 102 may formalize the health care cohort. For example, the health care cohort may be verified for further use. In a situation where one or more change inputs are received, the cohort creator 118 may redefine and/or reorganize the health care cohort. For example, the cohort creator 118 may update the health care cohort information. For instance, the cohort creator 118 may add one or more parameters to the health care cohort information and/or may remove one or more parameters from the health care cohort information. In some approaches, the cohort creator 118 may apply the change(s) indicated by the change input(s).

Additionally or alternatively, the cohort creator 118 may determine one or more primary intervention parameters, one or more acceptable secondary intervention parameters and/or one or more exclusionary secondary intervention parameters. For example, if an input change indicated an addition of an encounter, the cohort creator 118 may broaden the health care cohort by adding one or more parameters to the primary intervention and/or to the acceptable secondary intervention(s) (and/or by removing one or more parameters from the exclusionary secondary intervention(s)) in order to include the encounter. Additionally or alternatively, if an input change indicated a removal of an encounter, the cohort creator 118 may narrow the health care cohort by removing one or more parameters from the adding one or more parameters to the exclusionary secondary intervention(s) (and/or by removing one or more parameters from the primary intervention and/or from the acceptable secondary intervention(s)) in order to exclude the encounter. In some configurations, the cohort creator 118 may repeat (e.g., iterate) verification, redefinition and/or reorganization operations until the health care cohort is verified (e.g., until no change inputs are received and/or until an approval for the health care cohort is received via the user interface 114, for example).

The cohort creator 118 may clean the health care cohort data. For example, the cohort creator 118 may identify one or more data quality issues and resolve the one or more data quality issues. Data quality issues may include conflicts and/or inconsistencies in one or more health care cohort encounters. For example, a provider specialty may not match a health care intervention in an encounter (e.g., a podiatrist would not have performed neurological surgery), dates may conflict (e.g., a discharge date occurs before an admittance date), billing costs may conflict with the health care intervention, etc. In a situation that one or more data quality issues are identified, the cohort creator 118 may resolve the issue(s) and/or may remove one or more encounters with the issue(s) from the health care cohort. More detail is given in connection with one or more of FIGS. 4 and 7-9.

In some configurations, the cohort creator 118 may create one or more health care cohort tables. For example, the cohort creator 118 may populate one or more database tables based on the cleaned health care cohort (e.g., prehort) data. For instance, the cohort creator 118 may add one or more health care cohort encounters to one or more EDW tables. In some approaches, the cohort creator 118 may search one or more databases (e.g., an EDW) to find one or more encounters to include in the health care cohort. This may be in addition to the preliminary extraction performed previously. In some configurations, the health care cohort may be established when encounters are added to a health care cohort table. For example, a health care prehort may be converted to a health care cohort when the characteristics (e.g., primary intervention definition, list of acceptable secondary interventions, and/or list of exclusionary secondary interventions, etc.) are established and encounters are added to the health care cohort table. In some configurations, one or more operations on data before the encounters are added to the health care cohort table may be performed on a preliminary health care cohort (e.g., prehort).

In some configurations, the cohort creator 118 may attempt to identify any data quality issues. For example, the cohort creator 118 may iterate cleaning operations until no data quality issues remain. The cohort creator 118 may provide the health care cohort to the report generator 120.

The processor 104 may include and/or implement a report generator 120. The report generator 120 may generate a report based on the health care cohort. The report may include outcomes, costs and/or supply utilization. For example, the report may include outcomes (e.g., readmissions within a period) for one or more health care cohorts. Additionally or alternatively, the report may include costs for one or more health care cohorts. For instance, the report may include an average cost for one or more health care cohorts. In one example, the report may include a list of specific health care cohorts (e.g., health care cohorts) organized relative to a cost variation per health care intervention compared to an average. Additionally or alternatively, the report may include supply utilization for one or more health care cohorts. For instance, the report may indicate supply types (e.g., bandages, dressings, tapes, implants, gloves, intravenous (IV) products, instruments, surgical supplies, sutures, syringes, needles, pharmaceuticals, housekeeping supplies, laboratory supplies, etc.). The report may be presented on the display(s) 112 (e.g., user interface), stored and/or transmitted to another device.

The report may be organized and/or filtered to illustrate comparisons of outcomes, costs and/or supply utilization with respect to one or more health care systems (e.g., a group of hospitals, clinics, surgical suites, offices, etc.), one or more sites (e.g., hospital(s)) and/or one or more health care providers (e.g., physician(s), surgeon(s), physician's assistant(s), nurse(s), etc.). For example, a report may illustrate a comparison of outcomes (e.g., readmissions within 30 days) between hospitals (or health care providers) for a health care cohort. For example, a report may illustrate a comparison of outcomes (e.g., readmissions within 30 days) between hospitals (or health care providers) for a health care cohort (e.g., laparoscopic appendectomy). Additionally or alternatively, a report may illustrate a comparison of costs between hospitals (or health care providers) for a health care cohort. Additionally or alternatively, a report may illustrate a comparison of supply utilization (e.g., number of bandages per encounter, etc.) between hospitals (or health care providers) for a health care cohort.

In some configurations, the report may be a site-specific report. For example, the report may illustrate metrics (e.g., outcomes, costs, supply utilization, etc.) that are specific to a site (e.g., hospital, surgical suite, clinic, etc.). For instance, the report may compare metrics between health care providers at a hospital. In some configurations, the report may be a health care provider-specific report. For example, the report may illustrate metrics (e.g., outcomes, costs, supply utilization, etc.) that are specific to a health care provider (e.g., hospital, surgical suite, clinic, etc.). For instance, the report may illustrate metrics for a health care provider over a number of encounters.

In some configurations, the report may be organized to prioritize potential for improvement. For example, a list of sites and/or health care providers in the report may be sorted such that the metric (e.g., readmission rate, cost per encounter, supply utilization, etc.) for a health care cohort proceeds from the highest in descending order. Additionally or alternatively, a report may illustrate the comparative metrics (e.g., best and/or average outcomes, lowest and/or average cost per encounter, most efficient and/or average supply utilization, etc.) in comparison with the metrics of one or more health care systems, sites, and/or health care providers. In some approaches, the report may provide additional detail associated with the comparative metrics. For example, the report may illustrate the types and/or numbers of supplies used in a best and/or average encounter scenario. In another example, the report may illustrate one or more reasons for readmission of one or more sites and/or health care providers in comparison with the reason(s) for readmission for a site and/or health care provider.

In some configurations, the report may include a trend graph. The trend graph may illustrate the cost trend over time for a specific health care cohort for a health care system, a site (e.g., hospital, clinic, etc.) and/or a health care provider.

In some configurations, the report may be interactive. For example, the report may be presented on the user interface 114. The user interface 114 may include controls for changing the organization and/or scope of a report. For example, the user interface 114 may receive one or more inputs that specify a selection of a specific health care intervention (e.g., health care cohort), a scope (e.g., site comparison, health care provider comparison, etc.), one or more metrics (e.g., outcomes, costs, supply utilization, etc.), a metric sorting (e.g., highest to lowest, lowest to highest, date, etc.), etc. In some configurations, the report may include one or more controls for selecting one or more alternative supplies. For example, the report may include a list of supplies for a particular health care cohort used by a health care system, site, and/or health care provider. The computing device 102 (e.g., report generator 120, user interface 114, etc.) may produce the control (e.g., drop down menu, list, radio buttons, etc.) which may illustrate a selection of one or more alternative supplies (and their associated cost(s), for example). In some configurations, the control may emphasize (e.g., highlight, illustrate in bold, italics, different font size, different color, etc.) a cheapest alternative supply and/or an alternative supply utilized in a comparative scenario (e.g., by a different health care provider, in a standard encounter, in a lowest cost encounter, etc.). This approach may illustrate supply changes that may reduce cost for a specific health care intervention. In some configurations, the report may include an inventory listing of one or more types of supplies. For example, the inventory listing may indicate one or more numbers of one or more types of supplies that are on hand (at one or more sites, hospitals, clinics, etc., for instance).

It should be noted that one or more of the elements or components of the computing device 102 may be combined and/or divided. For example, the health care cohort identifier 116, the cohort creator 118, and/or the report generator 120 may be combined. Additionally or alternatively, one or more of the health care cohort identifier 116, the cohort creator 118, and/or the report generator 120 may be divided into elements or components that perform a subset of the operations thereof.

Figure 2:
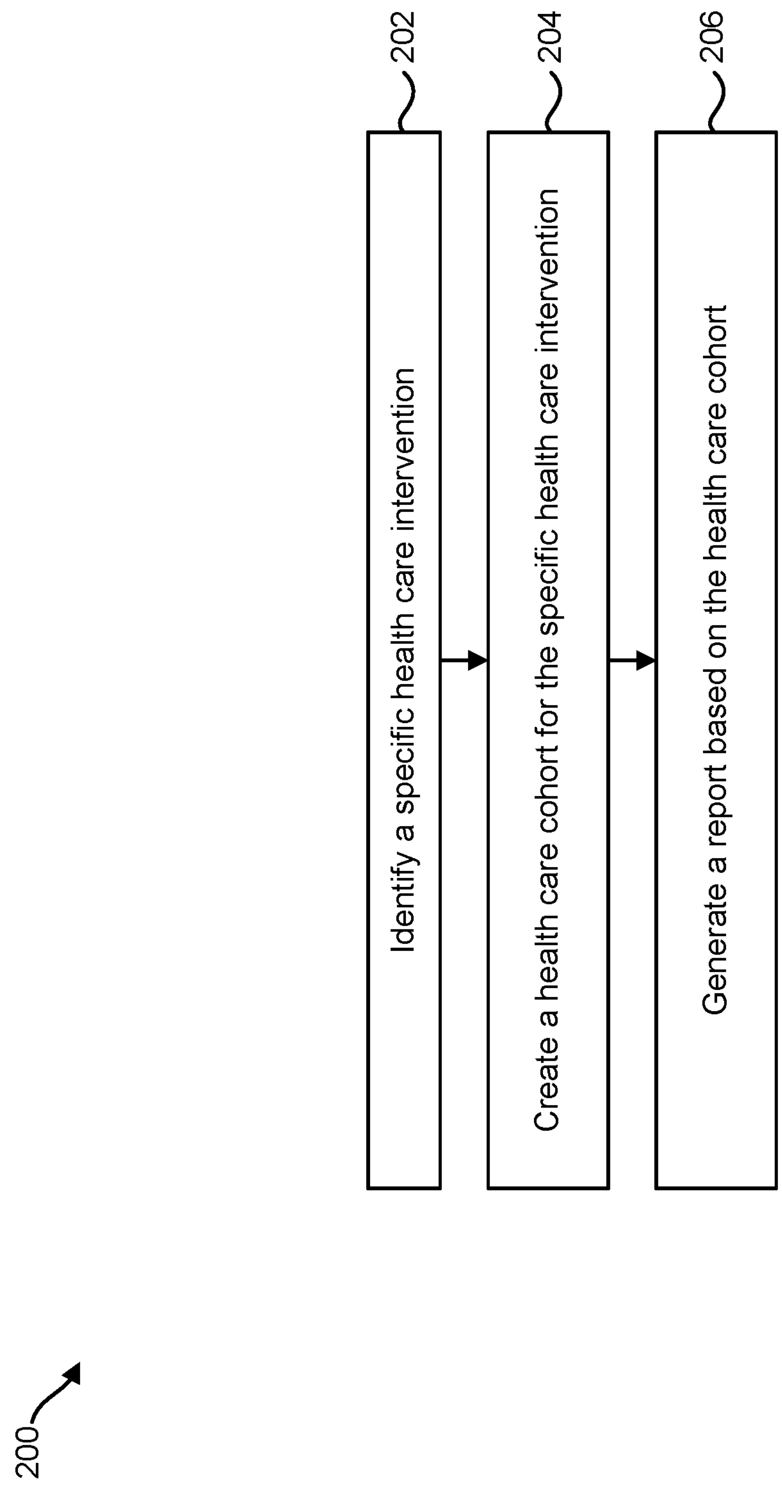
FIG. 2 is a flow diagram illustrating one configuration of a method for generating a report.

FIG. 2 is a flow diagram illustrating one configuration of a method 200 for generating a report. The method 200 may be performed by the computing device 102 described in connection with FIG. 1.

The computing device 102 may identify 202 one or more specific health care interventions. This may be accomplished as described in connection with one or more of FIGS. 1 and 3-4. For example, the computing device 102 may receive an input that specifies a specific health care intervention, may determine a primary intervention code that covers the specific health care intervention and/or may perform cost and/or encounter analysis in order to identify the specific health care intervention (e.g., to generate a suggested health care cohort).

The computing device 102 may create 204 one or more health care cohorts for the one or more specific health care interventions. This may be accomplished as described in connection with one or more of FIGS. 1 and 4-8, 10-11 and 13-14. For example, the computing device 102 may determine one or more encounters that are consistent with the health care cohort (e.g., consistent with the primary intervention, acceptable secondary intervention(s) and/or exclusionary secondary intervention(s), etc.). In some configurations, creating 204 the one or more health care cohorts may include extracting data, organizing the health care cohort and/or cleaning the health care cohort.

The computing device 102 may generate 206 a report based on the health care cohort. This may be accomplished as described in connection with one or more of FIGS. 1, 4, 9-10 and 12. For example, the computing device 102 may generate one or more reports that illustrate one or more health care intervention metrics (e.g., outcomes, costs, and/or supply utilization). Generating 206 the report(s) may include organizing the report(s) with respect to one or more health care systems, one or more sites and/or one or more health care providers. Additionally or alternatively, generating 206 the report(s) may include illustrating comparisons (of outcomes, costs and/or supply utilization, for example) based on one or more health care cohorts.

Figure 3:
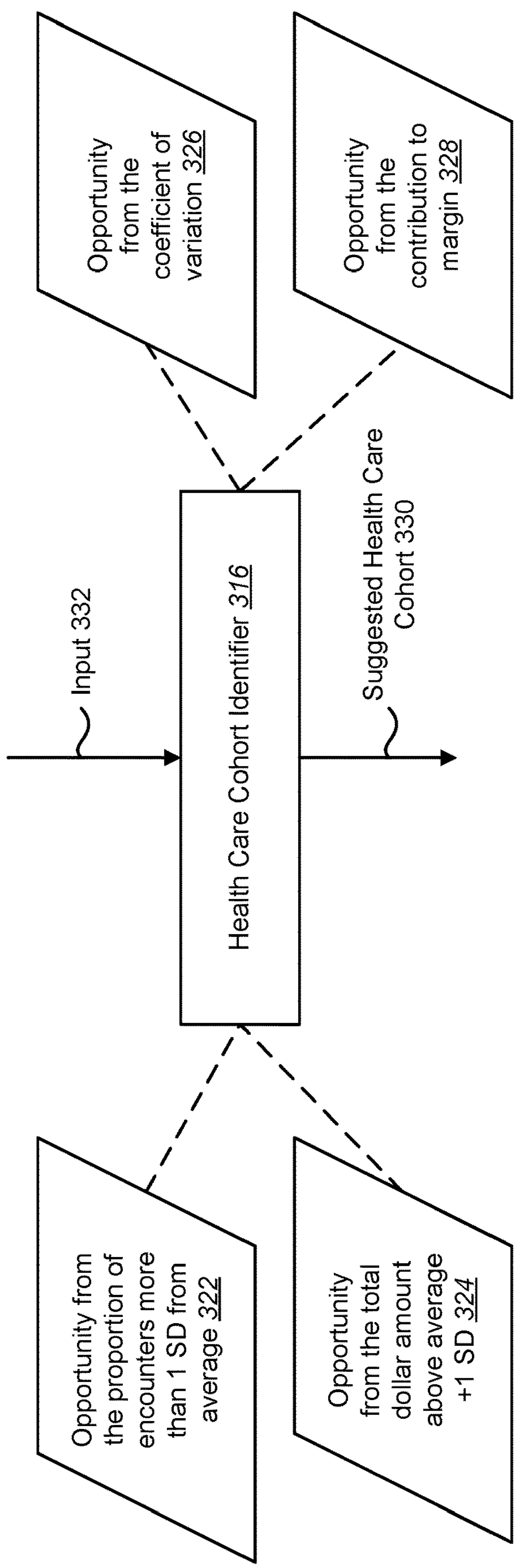
FIG. 3 is a block diagram illustrating an example of a health care cohort identifier.

FIG. 3 is a block diagram illustrating an example of a health care cohort identifier 316. The health care cohort identifier 316 may be one example of the health care cohort identifier 116 described in connection with FIG. 1. In this example, the health care cohort identifier 316 may determine a suggested health care cohort 330. One example of an analysis that may utilize a health care cohort is a hospital seeking reports comparing the cost of one intervention in a year to the cost of the intervention from the previous year.

If there is significant variation in the cost of an intervention from one time period to another, a hospital or health care provider team may look for ways to reconcile those cost differences and/or modify future decision making to better predict costs for patients and meet internal budget goals.

In some approaches, the health care cohort identifier 316 may receive input 332 from one or more users (e.g., a data management team and/or a team of health care providers). For example, reception of the input 332 may initiate the identification of a health care cohort. The input 332 may indicate a selected health care cohort and/or a selected health care intervention group. For instance, the health care cohort identifier 316 may select cost- and/or encounter-related analytics based on one or more existing health care intervention groups (e.g., groups of interventions based on one or more criteria, such as an ICD code and/or CPT code). Analytic considerations in this process may include, for example, searching one or more databases to find costs beyond a threshold, such as the opportunity from the total dollar amount above average+1 SD (more than one standard deviation) 324 or opportunity from the proportion of encounters more than 1 SD from the average 322. Further analytics may include opportunity from the coefficient of variation 326 and opportunity from the contribution to the margin 328, as illustrated in FIG. 3. For example, an "opportunity" may indicate health care cohort(s) with encounters with a given magnitude of cost difference amongst the encounters in the health care cohort.

One approach for developing a new health care cohort may involve an analytic review of a period of (e.g., the past several years') completed encounters for a selected health care intervention. The group of completed encounters may represent a group of patients, interventions and/or encounters that may be beneficial to analyze, obtain further detail on and/or form a health care cohort with. The health care cohort identifier 316 may create a set (e.g., list) of all additional interventions (e.g., secondary interventions) performed with the selected health care intervention. In some approaches, the health care cohort identifier 316 may present the set (e.g., list). For example, the set may be reviewed by a health care provider. The health care cohort identifier 316 may receive input 332, which may indicate which of those secondary interventions is considered appropriate to associate with the primary intervention. In some examples, developing a new health care intervention group may be initiated by reviewing encounters associated with a particular intervention that uses particular implants. Accordingly, the health care cohort identifier 316 may produce a suggested health care cohort 330 (e.g., a health care prehort) based on the one or more analytic considerations.

Figure 4:
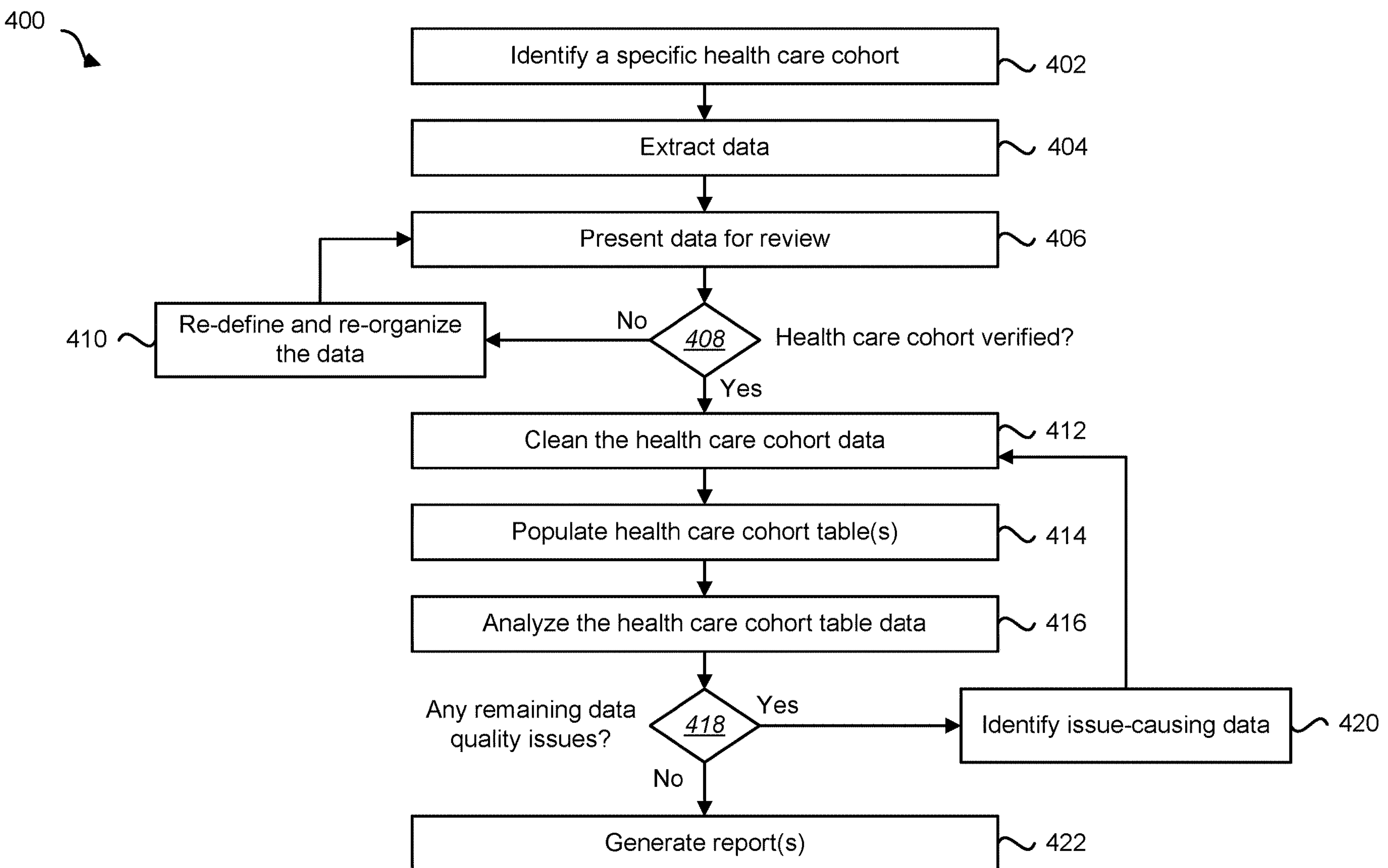
FIG. 4 is a flow diagram illustrating a more specific configuration of a method for generating a report.

FIG. 4 is a flow diagram illustrating a more specific configuration of a method 400 for generating a report. For example, the method 400 may include processing and refining health care intervention comparison data and generating a detailed analytic report. The method 400 may be performed by the computing device 102 described in connection with FIG. 1. The method 400 may be a more specific configuration of the method 200 described in connection with FIG. 2.

The computing device 102 may identify 402 a specific health care cohort. This may be accomplished as described in connection with one or more of FIGS. 1-3. For example, the computing device 102 may determine a suggested health care cohort (e.g., a health care prehort).

Once a suggested health care cohort has been obtained (as described in connection with FIG. 3, for example), the computing device 102 may extract 404 data (e.g., health care cohort data) from one or more databases (e.g., an EDW). This may be accomplished as described in connection with one or more of FIGS. 1 and 5. It should be noted that an EDW or a data warehouse (DW) may be utilized for reporting and data analysis. DWs may be central repositories of integrated data from one or more disparate sources. EDWs may store current and historical data and may be utilized for creating trending reports for senior management reporting such as annual and quarterly comparisons. The extracted data may provide definitions of populations that underwent the selected health care intervention, including an age range, gender and/or health complications, etc.

Once the population data has been extracted 404, the computing device 102 may present 406 the data for review. This may be accomplished as described in connection with one or more of FIGS. 1 and 5. For example, the computing device 102 may present the data on the display(s) 112 for review.

The computing device 102 may determine 408 whether the health care cohort is verified. This may be accomplished as described in connection with one or more of FIGS. 1 and 5. For example, the computing device 102 may determine whether any change input has been received. For instance, one or more users (e.g., data management team and/or health care provider(s), nurse, etc.) may review the data (e.g., health care prehort data) to see if the health care cohort and/or extracted data accurately reflect the specific health care cohort. In other words, the health care cohort may be verified in a situation that the data reflects a group of encounters for the specific health care cohort. In the situation that the computing device 102 receives one or more change inputs (e.g., the health care cohort is not verified) the computing device 102 may redefine and reorganize 410 the data and repeat presenting 406 the data for review. The computing device 102 may repeat determining 408 whether the health care cohort is verified. The computing device 102 may continue iterating these operations until the data reflects an accurate group of encounters for the specific health care cohort.

In a situation that the health care cohort is verified, the computing device 102 may clean 412 the health care cohort data. For example, the computing device 102 may clean and analyze the data and/or identify any data quality issues. Cleaning the data may include resolving any data quality issue(s) (e.g., fixing data errors) that may have occurred in the recording of the data. Examples of possible data errors or data quality issues are further described in connection with FIGS. 7 and 8. Examples may include, but are not limited to, the use of data from junked accounts or reused accounts, incomplete Medicare encounters, invalid costs, encounter dates that precede their admit date, wrong primary care provider assigned to an encounter, etc. Junked accounts may be remnants of joining the information together from two accounts (this sometimes happens with Medicare Patients, incapacitated patients, etc.).

The computing device 102 may populate 414 the health care cohort tables in one or more databases (e.g., one or more EDW tables) (once the health care cohort data has been cleaned 412, analyzed and/or any data quality issues have been identified, for example). This may be accomplished as described in connection with FIG. 1. For example, the computing device 102 store one or more encounters corresponding to the health care cohort in the EDW.

The computing device 102 may analyze 416 the data from the health care cohort tables. For example, the computing device 102 may attempt to identify any remaining data quality issues from the health care cohort tables. For instance, analyzing 416 the health care cohort table data may be performed similarly to the data analysis described above for the health care prehort data. In some configurations, the computing device 102 may present the health care cohort table data for review. In these configurations, the computing device 102 may receive one or more change inputs and/or one or more input indications of data quality issues. Accordingly, the computing device 102 may analyze the health care cohort table data automatically and/or optionally may receive input that indicates one or more data quality issues.

The computing device 102 may determine 418 whether any data quality issue(s) remain. For example, in a situation that analyzing 416 the health care cohort table data indicates one or more data quality issues, the computing device 102 may identify 420 issue-causing data. For example, the computing device 102 may mark (e.g., tag, label, record, etc.) the data in the health care cohort table data that is causing the data quality issue(s). The computing device 102 may repeat cleaning 412 the health care cohort data. For example, the computing device 102 may resolve the identified data quality issue and/or remove the issue-causing data (e.g., encounter).

In a situation that there are no remaining data quality issues, the computing device 102 may generate 422 a report (e.g., an analytic report 422). This may be accomplished as described above in connection with one or more of FIGS. 1-2.

Figure 5:
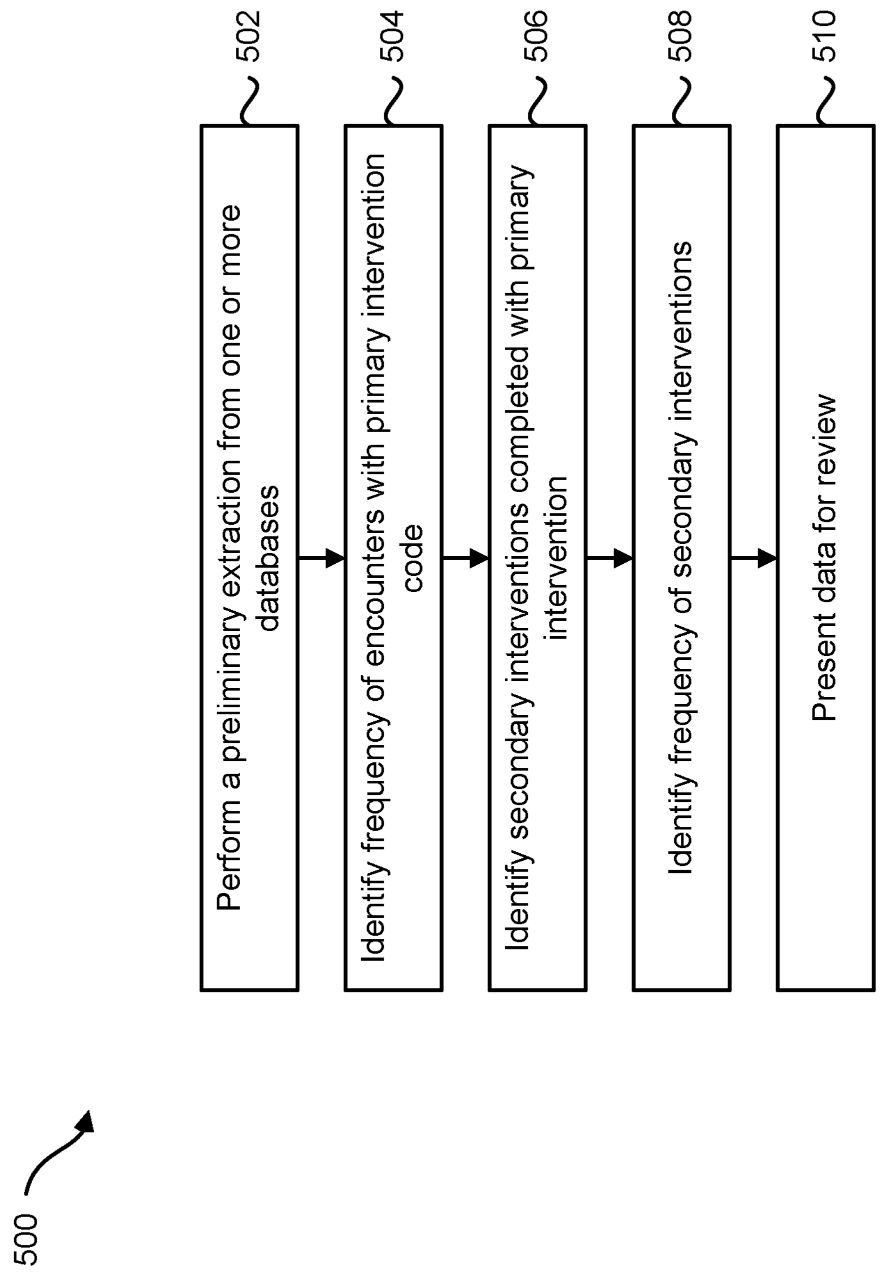
FIG. 5 is a flow diagram illustrating one configuration of a method for extracting health care cohort data.

FIG. 5 is a flow diagram illustrating one configuration of a method 500 for extracting health care cohort data. The method 500 may be performed by the computing device 102 described in connection with FIG. 1. For example, one or more of the operations described in connection with FIG. 5 may be performed by the cohort creator 118 described in connection with FIG. 1. Additionally or alternatively, one or more of the operations (e.g., steps) of the method 500 may be performed as part of and/or in conjunction with extracting 404 the data and/or presenting 406 the data for review as described in connection with FIG. 4.

The computing device 102 may perform 502 a preliminary extraction from one or more databases. For example, the computing device 102 may perform 502 a preliminary extraction of data (e.g., encounters) with the primary intervention code from the EDW. As described above, the primary intervention code may be received by the computing device 102 (as input from a user, for example) and/or may be identified by the computing device 102. The primary intervention code may be coding terminology (e.g., ICD code, CPT code, etc.) used by one or more national health care registries. One or more parameters (e.g., code(s), database(s), data range(s), etc.) may be utilized in performing 502 the preliminary extraction. For example, performing 502 the preliminary extraction may be performed 502 with one or more codes and one or more databases (e.g., general hospital billing intervention codes from a patient registry database). In some approaches, one or more parameters for performing 502 the preliminary extraction may be received as input (from a user, health care provider, etc., for example). The preliminary extraction may be refined and/or constrained by one or more date ranges. For example, only data (e.g., health care interventions, encounters, etc.) completed since a specific date (e.g., Jan. 1, 2008, etc.) may be extracted.

In some configurations, the computing device 102 may identify 504 a frequency of encounters with the primary intervention code. For example, the computing device 102 may determine how often (e.g., number of encounters over a period of time) encounters with the primary intervention code tend to occur. It should be noted that erroneous changes may be made in health care information systems that lead to data quality issues. For example, if the hospital has a frequency 100 appendectomy surgeries a month for the last 12 months, and then the next 3 months the frequencies for appendectomies go to zero, this is more likely related to a data quality issue than the hospital really not providing any appendectomy surgeries.

In some configurations, the computing device 102 may identify 506 secondary interventions completed with the primary intervention. For example, the computing device 102 may determine one or more secondary interventions (e.g., general billing codes) that occur in the same encounters as the primary intervention.

In some configurations, the computing device 102 may identify 508 a frequency of secondary interventions. For example, the computing device 102 may determine how often (e.g., number of encounters over a period of time, a number of encounters out of the encounters with the primary intervention over the total number of encounters with the primary intervention, etc.) encounters with the secondary intervention(s) tend to occur.

In some configurations, the computing device 102 may present 510 the data for review. This may be accomplished as described in connection with one or more of FIGS. 1 and 4. For example, the preliminary data extracted and/or accompanying data (e.g., frequency of encounters with the primary intervention code, secondary interventions, frequency of secondary interventions, etc.) may be presented (e.g., presented on a display, printed, transmitted, etc.). As described in connection with FIG. 4, the computing device 102 may verify the health care cohort (e.g., health care prehort). The computing device 102 may receive one or more change inputs (e.g., in an encounter that a health care provider wants to remove one or more factors and/or add one or more factors to describe the health care cohort population). As described in connection with FIG. 4, the data may be redefined and/or reorganized based on one or more change inputs. The health care cohort (e.g., prehort) may be verified (e.g., no change inputs are received and/or approval is received). For example, a health care provider may not have any changes when the health care cohort (e.g., prehort) is representative of the desired health care cohort or specific health care intervention. In some configurations, the data may then be organized, as described in connection with one or more of FIGS. 1, 4 and 6.

Figure 6:
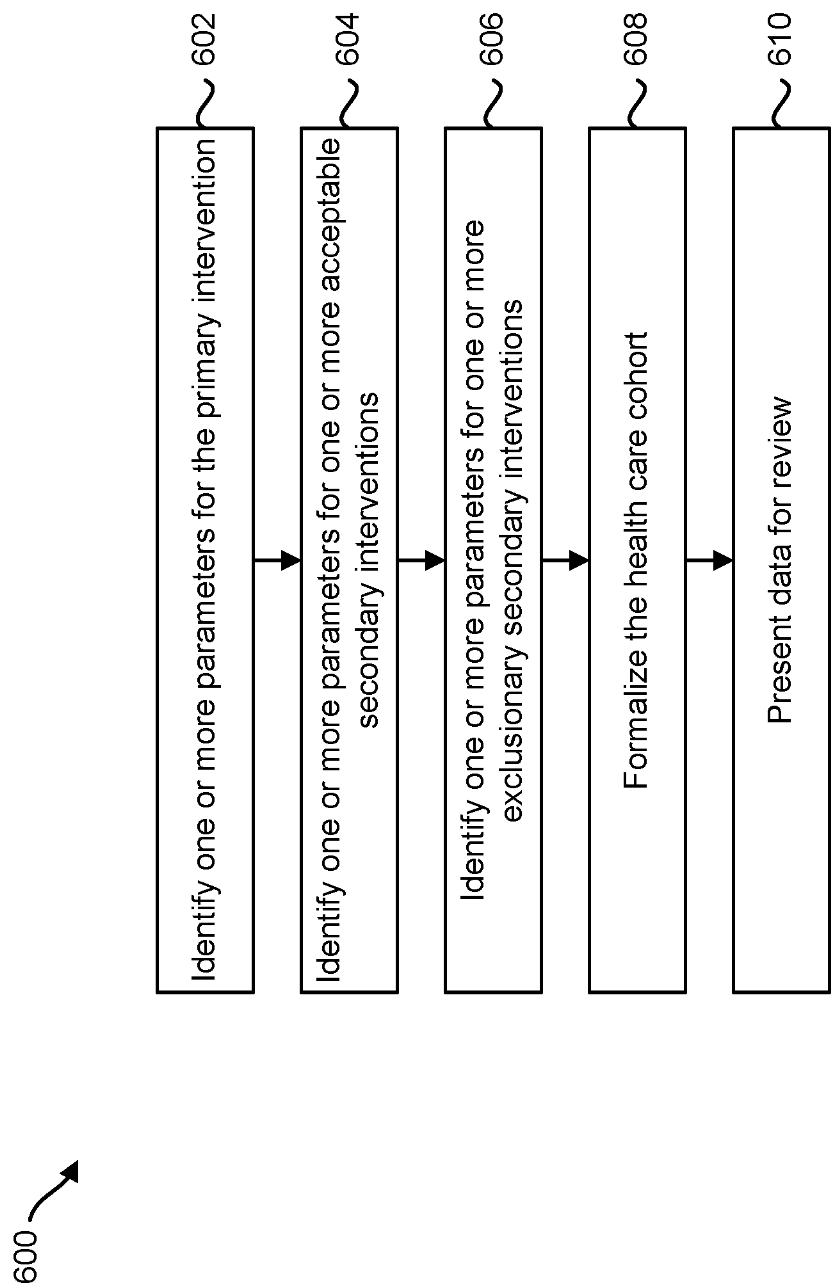
FIG. 6 is a flow diagram illustrating one configuration of a method for organizing a health care cohort.

FIG. 6 is a flow diagram illustrating one configuration of a method 600 for organizing a health care cohort. The method 600 may be performed by the computing device 102 described in connection with FIG. 1. For example, the method 600 may be performed as described in connection with FIG. 1. Organizing the health care cohort may include defining and/or redefine the health care cohort. As described herein, a health care cohort may offer more specificity than general health care intervention codes. For example, one health care intervention code may correspond to all appendectomies, including robotic appendectomies, laparoscopic appendectomies and open surgery appendectomies. For comparing costs, this data may not be accurately comparable since a robotic intervention may be significantly more expensive than the other types of interventions.

To organize a health care cohort, the parameters may be organized in one or more databases for a health care cohort. For example, the parameters may be organized into three categories: primary intervention definition parameters (e.g., mandatory code types), acceptable secondary intervention parameters (e.g., allowable code types), and/or exclusionary secondary intervention parameters (e.g., exclusionary code types). Organizing the health care cohort may be performed by the computing device 102 described in connection with FIG. 1. For instance, if an intervention is coded with a certain ICD procedure code, one or more rules (e.g., logic) may be utilized by the computing device 102 to include that encounter in a health care cohort. Many different rules (e.g., types of logic) may be utilized. In some configurations, the computing device 102 may receive input to add, remove and/or modify one or more parameters. The aforementioned three categories may include the same and/or different parameters. Some examples of parameters (e.g., intervention codes) that may be included in one or more of the categories may include one or more of the following parameters. Procedure codes may include International Classification of Diseases (ICD)-9 procedure codes, ICD-10 procedure codes and/or Current Procedure Terminology (CPT) codes, etc. Diagnosis codes may include ICD-9 diagnosis codes, ICD-10 diagnosis codes, and/or systemized nomenclature of medicine (SNOMED) Clinical Terms (CT), etc. SNOMED may be a standard (similar to ICD-10, for example), but may be specifically used by pathologist(s). A hospital information system intervention procedure code may be another example of a parameter. Billing groups may include internal charge codes, Diagnosis Related Groups (DRGs), All Patient Refined Diagnosis Related Groups (APRDRGs) and/or Medicare Severity Diagnosis Related Groups (MSDRGs), etc. Item types may include unspecified codes, explicitly state codes, similarly sounding items and/or item descriptions, etc. For example, item types may include codes such as United Nations Standards Products and Services Code (UNSPSC) codes, item description and/or internal classifications, etc. Registries may include the Society of Thoracic Surgery (STS) database, National Surgery Quality Improvement Project (NSQIP) and/or internal disease specific registries, etc. Comorbidity indices may include examples such as Charleson Comorbidity Index, Severity of Illness (SOI) and/or Risk of Mortality (ROM), etc. Provider specialty may be a health care provider specialty (e.g., physician specialty). Hospital descriptors may be hospital assigned codes including trauma level, patient status to include inpatient and outpatient and/or operating room level, etc. The number of surgeries may be the number of times a patient visited the operating room during a patient encounter. Patient demographics may include age, body mass index (BMI), weight, and gender. Clinical notes may include notes related to operative summary, discharge, admit, history and/or physical, etc. Clinical test results examples may include vital signs, pathology, laboratory results, and/or imaging results, etc.

It should be noted that fewer, more and/or alternative parameters may be utilized in some configurations. For example, any data element stored within an electronic medical record (EMR) may be utilized. It should be noted that utilizing many different coding terminologies from various institutions and health care providers may allow creating more specific, accurate, and/or homogenous health care cohorts for comparison than existing analytic products on the market.

The computing device 102 may identify 602 one or more parameters for the primary intervention. For example, the computing device 102 associate and/or store one or more parameters for the primary intervention definition. For instance, the computing device 102 may store an ICD code and a CPT code that specify a spinal fusion, a charge code that indicates a 2 level spinal fusion, an item description for a titanium plate used in 2 level spinal fusions and clinical note keywords (e.g., "2 level," "L2/L3," etc.) that may indicate a two level spinal fusion.

The computing device 102 may identify 604 one or more parameters for one or more acceptable secondary interventions. For example, the computing device 102 associate and/or store one or more parameters for any acceptable secondary intervention(s). For instance, the computing device 102 may store an ICD code specifies spinal stenosis and a CPT code that specifies laminectomy.

The computing device 102 may identify 606 one or more parameters for the primary intervention. For example, the computing device 102 associate and/or store one or more parameters for one or more exclusionary secondary interventions. For instance, the computing device 102 may store a charge code that indicates a 3 level spinal fusion, an item description for a titanium plate used in 3 level spinal fusions and clinical note keywords (e.g., "3 level," "L2/L3/L4," etc.) that may indicate spinal fusions other than 2 level spinal fusions.

The computing device 102 may formalize the health care cohort. This may be accomplished as described above in connection with FIG. 1. For example, the computing device 102 may indicate that the health care cohort is formalized (e.g., that the health care cohort is no longer a health care prehort).

The computing device 102 may present 610 data for review. This may be accomplished as described in connection with one or more of FIGS. 1 and 4. For example, the computing device 102 may present the organized health care cohort data on one or more displays 112 (e.g., on a user interface 114), may print the health care cohort data and/or may send the health care cohort data. As described herein, the computing device 102 may reorganize and/or redefine the health care cohort (e.g., parameters) if one or more change inputs are received. Alternatively, the computing device 102 may further use the health care cohort if no change inputs are received and/or if an input indicating health care cohort approval is received.

Figure 7:
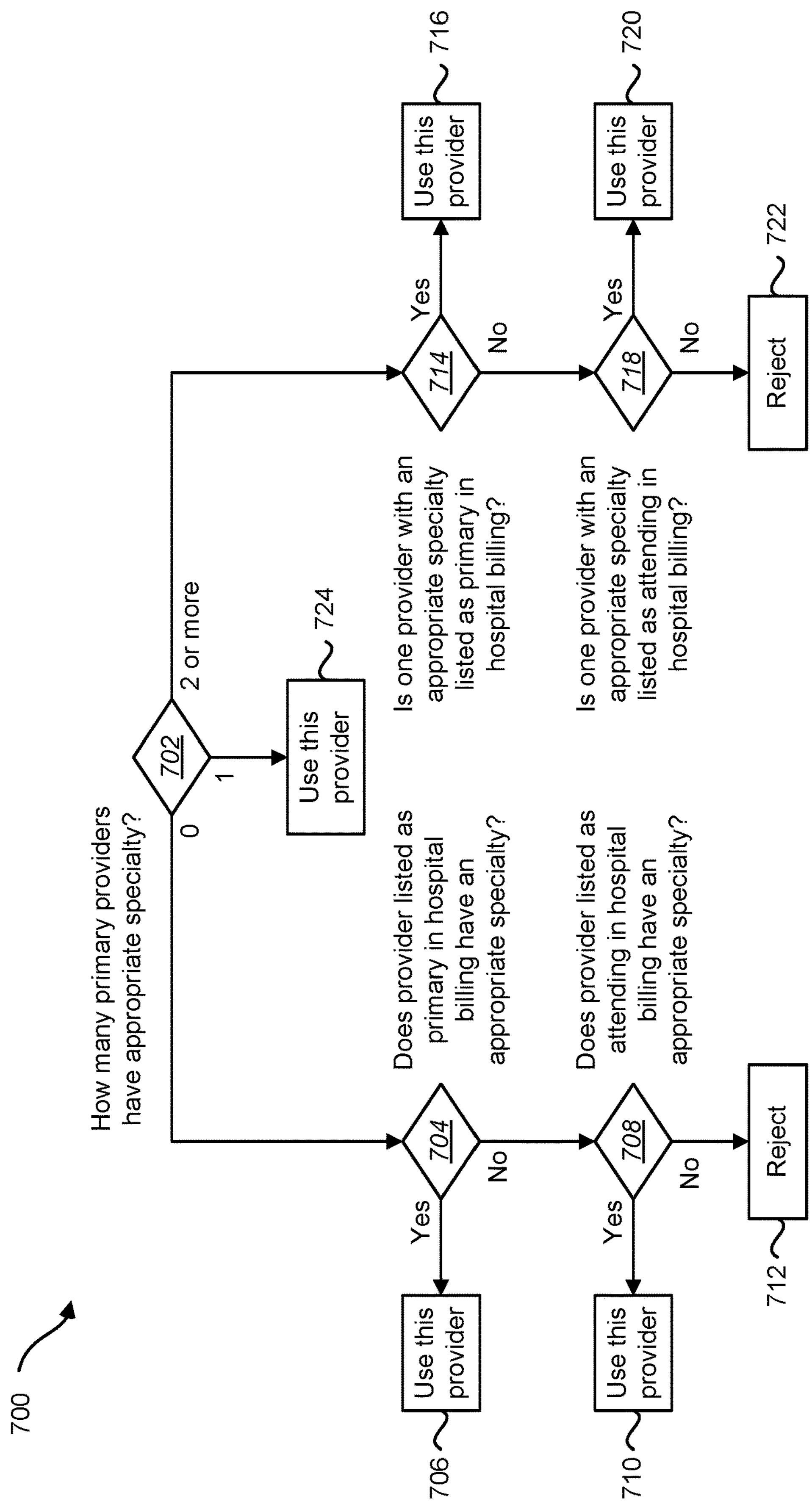
FIG. 7 is a flow diagram illustrating one configuration of a method for assigning a primary health care provider.

FIG. 7 is a flow diagram illustrating one configuration of a method 700 for assigning a primary health care provider (e.g., correct primary health care provider). For example, the method 700 may be performed as an example of and/or part of cleaning the health care cohort data as described in connection with one or more of FIGS. 1 and 4. In other words, the method 700 may be an example of analyzing data, identifying one or more data quality issues and/or resolving the one or more data quality issues. As described above, health care cohort data may contain errors, such as mistakes in the input and recording of the data. The method 700 may be performed in order to assign a correct primary health care provider. For example, a wrong surgeon may be associated with a particular encounter. For instance, if a patient had heart surgery, the method 700 may help to ensure that the surgeon assigned to the encounter had the specialty of cardio thoracic surgeon. If the associated surgeon for the cardiac encounter was a urologist, the encounter may not be accepted into the health care cohort.

In some approaches, cleaning health care cohort data may include identifying how many health care providers have a certain specialty in order to determine whether the correct primary provider is recorded for an encounter (e.g., health care intervention and/or patient). For example, data quality issues may be identified by determining whether a health care provider listed as a primary (e.g., primary provider) in hospital billing records has an appropriate specialty (for an encounter and/or a health care intervention, for instance).

The data may be rejected if the health care provider does not have the appropriate specialty.

Data relating to the assignment of a health care provider may need to be corrected if errors or data quality issues are discovered. Potential data quality issues may include, for example, a clerical error such as a wrong health care provider having been assigned to an encounter, or two health care providers with the same name but different specialties being mistaken in the health care provider assigning process. Some data may need to be removed from the health care cohort population if an error is identified and rejected in this process.

The method 700 described in connection with FIG. 7 may be performed by the computing device 102 described in connection with FIG. 1, for example. The computing device 102 may determine 702 how many providers (e.g., primary providers) have an appropriate specialty (for a specific health care intervention and/or for the health care cohort, for instance). For example, the computing device 102 may identify one or more appropriate specialties for performing a specific health care intervention. In some approaches, the computing device 102 may request and/or receive the appropriate specialty(ies) for performing the specific health care intervention. For example, the computing device 102 may receive one or more appropriate specialties from one or more databases (e.g., an EDW) and/or from input. An appropriate specialty is a specialty that is qualified to perform the specific health care intervention. For example, a health care provider with a neurosurgery specialty may be qualified to remove a brain tumor but a health care provider with a podiatry specialty may not be qualified to remove a brain tumor. The computing device 102 may determine 702 how many (e.g., a number of) primary providers that have one or more of the appropriate specialties. For example, the computing device 102 may determine the number of primary health care providers (for an encounter, for example) that have an appropriate specialty for performing the specific health care intervention.

In a situation that zero primary providers have the appropriate specialty, the computing device 102 may determine 704 whether the provider listed as a primary in hospital billing records has an appropriate specialty. For example, the computing device 102 may look up the specialty(ies) of the health care provider listed as a primary health care provider in the hospital billing records (in one or more databases, for example). If the specialty of the primary health care provider matches the appropriate specialty (e.g., at least one of the appropriate specialties), the computing device 102 may use 706 that provider (e.g., may associate that provider with the encounter in the health care cohort).

If the provider listed as the primary in hospital billing records does not have an appropriate specialty, the computing device 102 may determine 708 whether the provider listed as attending in hospital billing records has an appropriate specialty. For example, the computing device 102 may look up the specialty(ies) of the health care provider listed as an attending health care provider in the hospital billing records (in one or more databases, for example). If the specialty of the attending health care provider matches the appropriate specialty (e.g., at least one of the appropriate specialties), the computing device 102 may use 710 that provider (e.g., may associate that provider with the encounter in the health care cohort). If the specialty of the attending health care provider does not match the appropriate specialty (e.g., any of the appropriate specialties), the computing device 102 may reject 712 the data. For example, the computing device 102 may remove the encounter from the health care cohort.

In a situation that one provider has the appropriate specialty, the computing device 102 may use 724 that provider. For example, the computing device 102 may associate that provider with the encounter in the health care cohort.

In a situation that two or more providers have the appropriate specialty, the computing device 102 may determine 714 whether one provider with an appropriate specialty is listed as a primary in hospital billing records. For example, the computing device 102 may look up the specialty(ies) of the health care providers listed as primary health care providers in the hospital billing records (in one or more databases, for example). If the specialty of one (e.g., only one) of the primary health care providers matches the appropriate specialty (e.g., at least one of the appropriate specialties), the computing device 102 may use 716 that provider (e.g., may associate that provider with the encounter in the health care cohort).

If the providers listed as primary in hospital billing records do not have an appropriate specialty, the computing device 102 may determine 718 whether one provider with an appropriate specialty is listed as attending in hospital billing records. For example, the computing device 102 may look up the specialty(ies) of the health care provider(s) listed as an attending health care provider in the hospital billing records (in one or more databases, for example). If the specialty of the attending health care provider matches the specialty (e.g., at least one of the appropriate specialties), the computing device 102 may use 720 that provider (e.g., may associate that provider with the encounter in the health care cohort). If the specialty of the attending health care provider (s) does not match the specialty (e.g., any of the appropriate specialties), the computing device 102 may reject 722 the data. For example, the computing device 102 may remove the encounter from the health care cohort.

Figure 8:
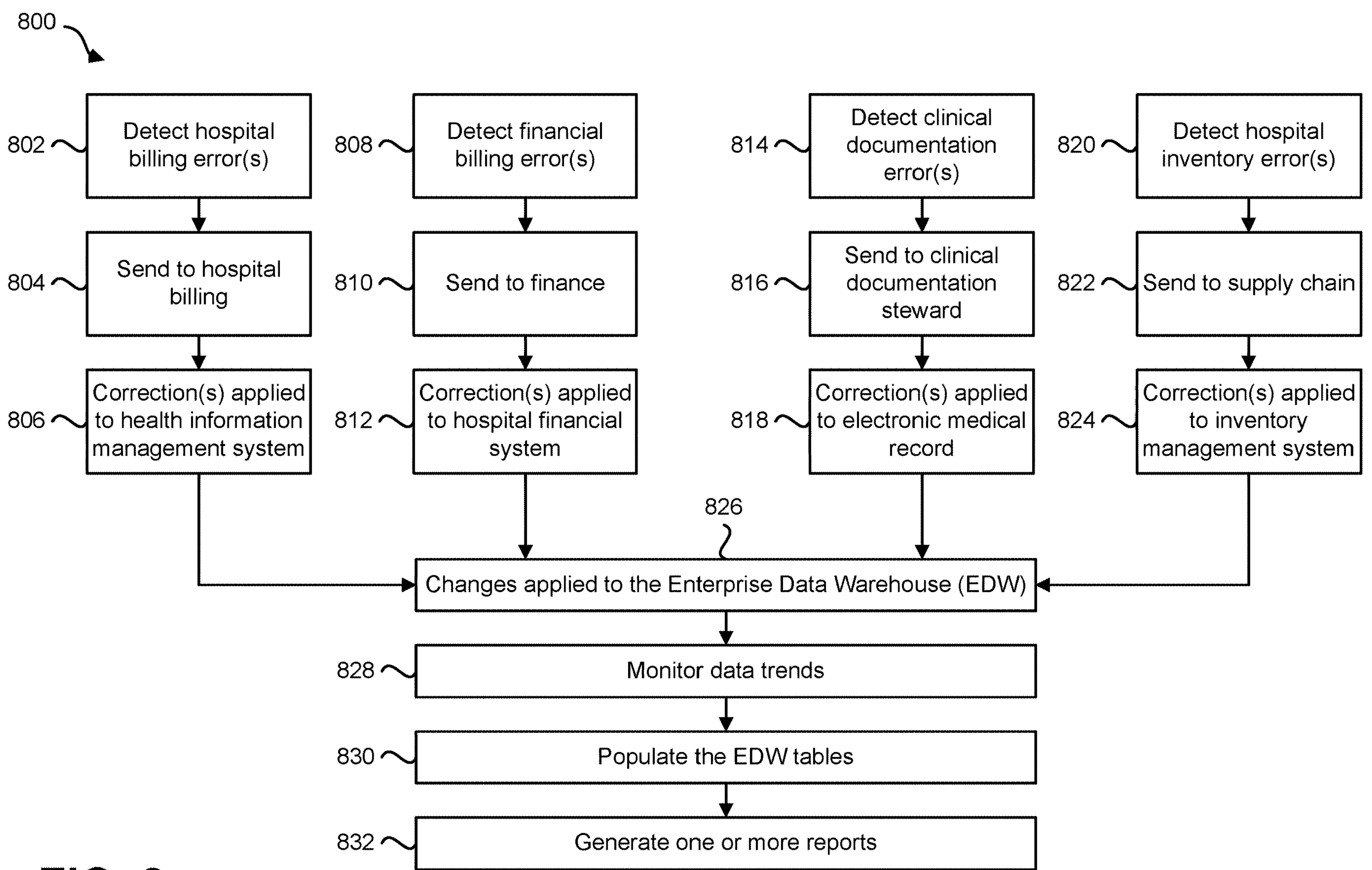
FIG. 8 is a flow diagram illustrating a configuration of a method for cleaning data.

FIG. 8 is a flow diagram illustrating a configuration of a method 800 for cleaning data (e.g., actively monitoring for data inconsistencies to identify and take corrective action). In some approaches, some data quality issues may be sent for correction. For example, different data quality issues may originate from different sources. The data may be sent to another system for review and resolution.

One or more of the operations of the method 800 may be performed by the computing device 102 described in connection with FIG. 1. Additionally or alternatively, one or more of the operations of the method 800 may be performed by another system (e.g., a remote electronic device from another department and/or entity of a health care system). Some hospital billing errors may include examples such as junked accounts, reused accounts, incomplete Medicare encounters (e.g., I42s), merged Enterprise Master Patient Index (EMPI), and a discharge date before the admit date. The computing device 102 may detect 802 one or more hospital billing errors. The computing device 102 may send 804 the hospital billing errors. For example, the hospital billing errors may be sent to a hospital billing system (e.g., health information management system). One or more corrections may be applied 806 to the health information management system. Corresponding changes may be applied 826 to the EDW.

Financial billing errors may include errors such as invalid costs and may be resolved by the hospital financial system. For example, an invalid cost may occur when the hospital cost for the encounter is more than the hospital charge for the encounter. This may typically represent a data error. The computing device 102 may detect 808 one or more financial billing errors. The computing device 102 may send 810 the financial billing errors. For example, the financial billing errors may be sent to a finance system. One or more corrections may be applied 812 to the hospital financial system. Corresponding changes may be applied 826 to the EDW.

Clinical documentation errors may include examples such as the account number not joining to the electronic medical record, encounter date before admit date, encounter date before discharge and wrong specialty for provider, etc. An encounter may be a record with a unique number assigned to a patient when they have an interaction (e.g., hospital stay) with a health care provider and/or facility. An encounter may help track all the activities that occurred to the patient during their stay. For example, health care data may be stored in different databases. Radiology may have a radiology database that is separate from a laboratory database that houses laboratory data. In some instances, these databases may get out of sync. For example, Patient A may have encounter 12345 in the radiology database, but the same Patient A has encounter number 5678 in the laboratory database. The databases should have the same encounter number for Patient A, but have different encounter numbers. Accordingly, when attempting to determine a patient's total cost for a hospital stay, the radiology data may not join with the laboratory data. Accordingly, the two medical records may not be joined because of the encounter number differences. Corrections may be made within the electronic medical record. The computing device 102 may detect 814 one or more clinical documentation errors. The computing device 102 may send 804 the clinical documentation errors. For example, the clinical documentation errors may be sent to a clinical documentation steward system. One or more corrections may be applied 818 to the electronic medical record. Corresponding changes may be applied 826 to the EDW.

Hospital inventory errors may include no material management. Inventory data may be corrected by the inventory management system (e.g., purchasing department). The computing device 102 may detect 820 one or more hospital inventory errors. For example, hospital inventory errors may be detected 820 in material management data. Material management data may include supplies and/or items. For instance, material management data may be stored in a specific database that deals with the supplies or items that are used for the patient care during their hospital stay (e.g., scalpels, oxygen tubes, sheets, gowns, gloves, etc.). The computing device 102 may send 822 the hospital inventory errors. For example, the hospital inventory errors may be sent to a supply chain system. One or more corrections may be applied 824 to the supply chain system (e.g., inventory management system). Corresponding changes may be applied 826 to the EDW.

In addition to or alternatively from other systems correcting errors, the computing device 102 may clean the data (e.g., correct one or more errors) using a specific code or algorithm. One example is given in connection with FIG. 7. Additionally or alternatively, the EDW may clean data and/or reorganize the data using a specific code or algorithm. For example, the EDW may execute logic in order to collect data, clean data and/or organize the data into one or more health care cohorts. The algorithm may include one or more processes described herein for obtaining data (e.g., encounter data, etc.) and/or organizing the data for reporting.

The computing device 102 may monitor 828 data trends. For example, the computing device 102 (e.g., report steward) may perform ongoing data trend surveillance for the appropriateness of the errors being sent for resolution. For example, generating reports may depend on a flow of data from one or more data sources. In some instances, something may change in a data source to cause the data to stop flowing. For example, a health care cohort may be defined by an ICD procedure code and corresponding data may populate one or more database tables. The computing device 102 may detect (upon a certain date, after a length of time, for example) that new records for health care cohorts defined by an ICD code has not been received. The computing device 102 may indicate that something has changed that prevents one or more health care cohorts from being updated. For example, one cause of such a problem may be that an intervention is no longer coded with ICD-9 codes, but with ICD-10 codes instead. In some configurations, the computing device 102 may update the definition of one or more health care cohorts to include ICD-10 codes. Other systems (e.g., hospitals) may identify different types of data errors in some approaches.

The computing device 102 may populate 830 the EDW tables (with the corrected EDW data, for example). For example, once the corrections have been applied to the EDW, the data can be used to populate the health care cohort tables in the EDW in order to generate more accurate reports. The computing device 102 may generate 832 one or more reports (e.g., analytic reports). This may be accomplished as described in connection with one or more of FIGS. 1-2, 4, 9-10 and 12.

Figure 9:
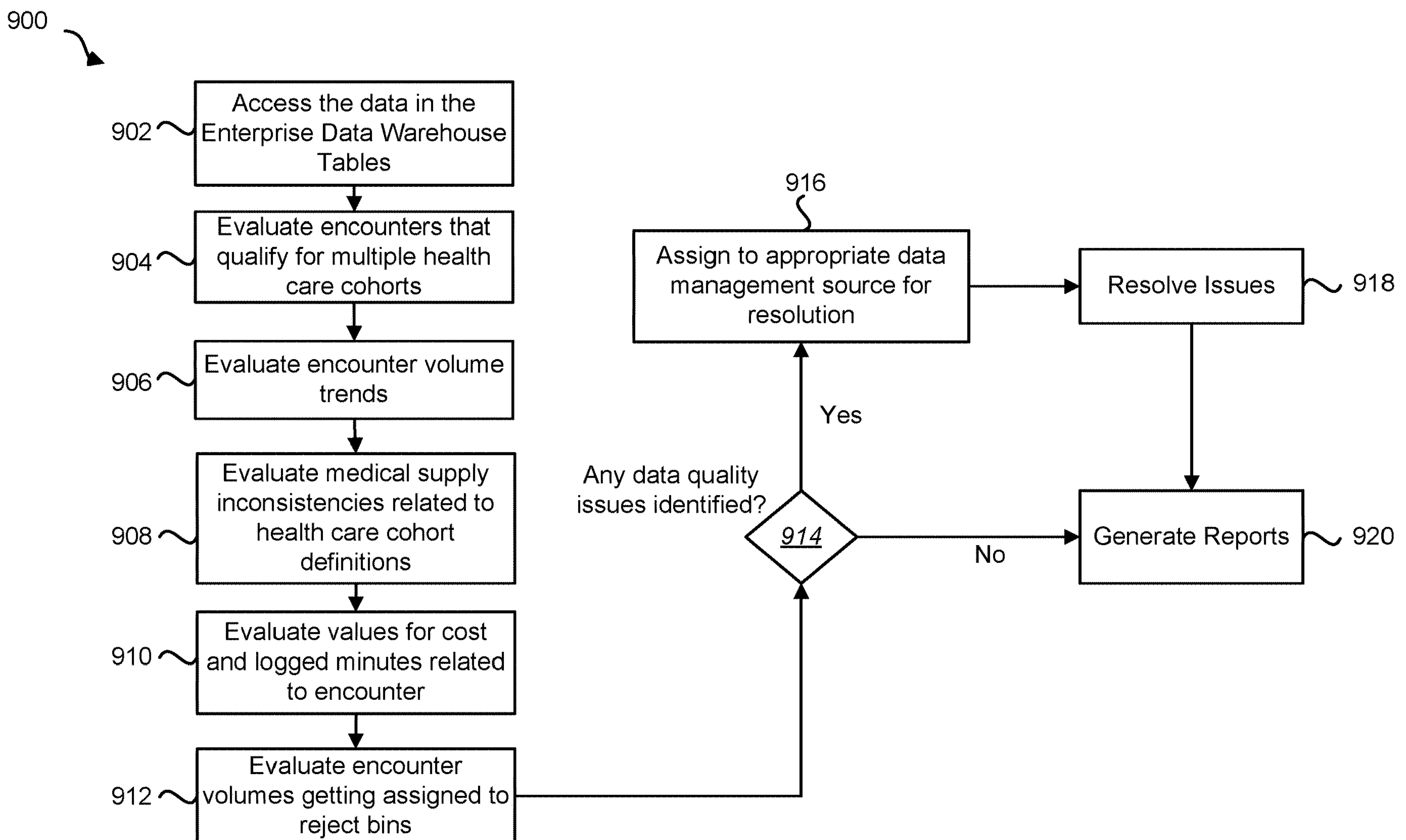
FIG. 9 is a flow diagram illustrating a method for analyzing data trends in database tables.

FIG. 9 is a diagram illustrating a method 900 for analyzing data trends in database (e.g., EDW) tables. The method 900 may be one example of the process of analyzing 416 data described in connection with FIG. 4. The method 900 may be performed by the computing device 102 and/or one or more electronic devices 110 described in connection with FIG. 1. The method 900 may enable monitoring data for issues that may qualify an encounter for multiple health care cohorts. For example, the method 900 may include identifying and/or resolving one or more issues. In some configurations, identified issue(s) may be presented to a user (e.g., a data management team).

The computing device 102 may access 902 the data in the Enterprise Data Warehouse (EDW) tables. For example, the computing device 102 may access (e.g., search, request, retrieve, etc.) data from one or more EDW tables. The data may indicate one or more encounters. An encounter may be a record (with a unique number, for example) of an interaction between a health care provider and a patient.

The computing device may evaluate 904 encounters that qualify for multiple health care cohorts. For example, the computing device 102 may determine whether any encounters are included in multiple health care cohorts. For instance, the assignment of primary and secondary interventions for an encounter may have errors that allow an encounter to qualify for multiple health care cohorts. In some instances, two health care cohort definitions may be similar enough that a patient's encounter can meet the criteria to be in both health care cohorts. In some configurations, encounters may be sent to an appropriate data steward system. For example, a data steward system may be a system that collects and processes data. In some configurations, the data steward may present encounter data to one or more users for review. Additionally or alternatively, the data steward system may resolve one or more issues and/or receive input with corrections for resolving one or more issues.

The computing device 102 may evaluate 906 encounter volume trends. For example, the computing device 102 may determine how often a health care intervention is being performed over time and/or may determine whether the health care intervention is being performed with or without one or more additional interventions. For instance, ongoing surveillance evaluates encounter volume trends, such as if an intervention is being done less frequently or now is done with or without an additional intervention. In some configurations, evaluating 906 encounter volume trends may include assessing for inconsistencies within health care cohorts and/or health care exhorts, by facility, by primary surgeon, by month and/or by year.

The computing device 102 may evaluate 908 medical supply inconsistencies related to health care cohort definitions. For example, the computing device 102 may determine when a particular medical supply may be missing from an encounter.

The computing device 102 may evaluate 910 values related to health care encounter(s). For example, the computing device 102 may evaluate values for cost and/or logged minutes related to the health care encounter(s) (e.g., health care cohort). For example, the computing device 102 may monitor for changes occurring to one or more health care cohorts. For instance, if over the last 5 years the average operating room (OR) time for appendectomies is 100 minutes and then in the last two month the average OR time doubles to 200 minutes, the computing device 102 may provide an indication that an investigation of the sudden increase may be beneficial.

The computing device 102 may evaluate 912 encounter volumes getting assigned to reject bins. For example, the computing device 102 may determine encounters that are getting assigned to reject bins to identify data trends.

The computing device 102 may determine 914 whether any data quality issues were identified. For example, the computing device 102 may determine 914 whether any of the evaluations 904, 906, 908, 910, 912 identified any issues.

If the computing device 102 determines 914 that one or more data quality issues were identified, the computing device 102 may assign 916 the issue(s) to an appropriate data management source for resolution. For example, the computing device 102 may send (e.g., return) one or more encounters for resolution by the billing and/or clinical documentation steward system(s).

The computing device 102 may resolve 918 the one or more issues. For example, the computing device 102 may make one or more automatic corrections, may make one or more corrections based on an input and/or may receive one or more corrections. The computing device 102 may generate 920 one or more reports (based on the corrected data, for example). This may be accomplished as described in connection with one or more of FIGS. 1-2, 4, 8, 10, 12 and 14. It should be noted that if any data quality issues are identified in this analysis of data in the EDW tables, one or more processes of the method 900 of resolving the issues may repeat by cleaning and analyzing the data (as described in connection with one or more of FIGS. 1-2, 4 and 7-8, for example) If no data quality issues are identified, the computing device 102 may generate 920 reports.

Figure 10:
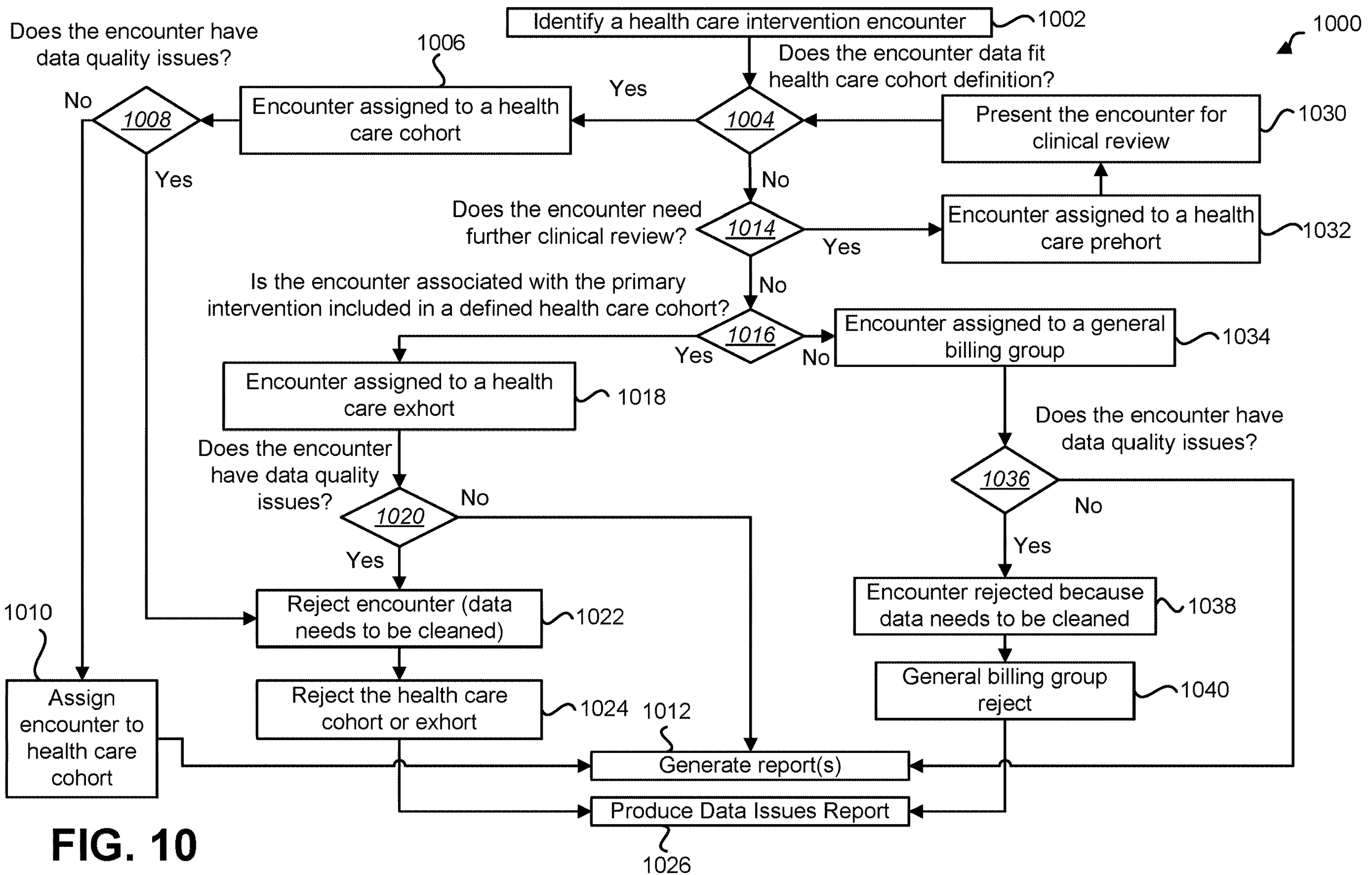
FIG. 10 is a flow diagram that illustrates a more specific configuration of a method for analyzing data to determine data quality issues.

FIG. 10 is a flow diagram that illustrates a more specific configuration of a method 1000 for analyzing data to determine data quality issues (e.g., analyzing encounters). The method 1000 may be performed by the computing device 102 and/or one or more electronic devices 110 described in connection with FIG. 1. The computing device 102 may identify 1002 an encounter (e.g., medical encounter). For example, the computing device 102 may access the EDW to identify an encounter.

The computing device 102 may determine 1004 whether the encounter data (e.g., data corresponding to the encounter) fits the health care cohort definition. For example, the computing device 102 may determine whether the encounter data indicates a primary intervention, one or more acceptable secondary interventions, and/or one or more exclusionary secondary interventions.

If the computing device 102 determines 1004 that the encounter fits the definition of a health care cohort, the computing device 102 may assign 1006 the encounter to a health care cohort. For example, the computing device 102 may add the encounter to the health care cohort (e.g., store the encounter in a health care cohort table).

The computing device 102 may determine 1008 whether the encounter has data quality issues. For example, it may be beneficial to determine if the encounter fits into the health care cohort but still has data quality issues. This may be accomplished as described in connection with one or more of FIGS. 1-2, 4 and 7-9, for instance. If the encounter does not have data quality issues, the computing device 102 may assign 1010 the encounter to the health care cohort. For example, the computing device 102 may store the encounter in a health care cohort table. The computing device 102 may generate 1012 one or more reports (e.g., analytic reports) based on the health care cohort. This may be accomplished as described in connection with one or more of FIGS. 1-2, 4, 8-9, 12 and 14, for instance. For example, if the encounter does not have data quality issues, the encounter may be assigned 1010 to the health care cohort and included within an analytic report.

If the computing device 102 determines 1008 that the encounter fits a definition of a health care cohort but has quality issues, the computing device 102 may reject 1022 the encounter (because the data needs to be cleaned, for example) and/or may reject 1024 the health care cohort. For example, the computing device 102 may not utilize the encounter as valid data. The computing device 102 may produce 1026 a data issues report. For example, the computing device 102 may generate a report that indicates one or more encounters, health care cohorts, health care exhorts, and/or general billing groups with data quality issues.

If the computing device 102 determines 1004 that the encounter does not fit the definition of a health care cohort, the computing device 102 may determine 1014 whether the encounter needs further clinical review. For example, the computing device 102 may determine whether the encounter meets criteria for inclusion in a defined health care cohort or needs to be flagged for further review. Additionally or alternatively, the computing device 102 may make this determination 1014 based on one or more rules (e.g., flag all encounters that do not fit a health care cohort definition, flag non-health care cohort encounters from a particular clinic/health care provider, etc.).

If the computing device 102 determines 1014 that the encounter needs further clinical review, the computing device 102 may assign 1032 the encounter to a preliminary health care cohort. For example, the computing device 102 may store the encounter in a preliminary health care cohort table. In some instances, data for classifying encounters into health care cohorts may be incomplete. Take spine surgery, for example. The ICD procedure codes may classify all surgeries with 2 to 8 levels of fusion in the same code. The cost for a 2 level spinal fusion is quite different than an 8 level fusion. In this situation, spine encounters may be loaded into a health care cohort refiner (e.g., cohort extractor). Additional codes may be added to these encounters in order to differentiate all the levels of fusions into their own health care cohort. So, instead of having one health care cohort with spinal fusions for 2 to 8 levels, there may be 8 health care cohorts specified by their spinal fusion level (2 level, 3 level, 4 level, 5 level, etc.). Some approaches to refining health care cohorts are given in connection with FIG. 14.

The computing device 102 may present 1030 the encounter for clinical review. For example, the computing device 102 may display the encounter data and/or may send the encounter data to a user (e.g., health care provider, etc.). In some configurations, the computing device 102 may search all clinical documentation for consistent data elements. Take spinal fusions, for example. One hundred encounters with varying levels of spinal fusions may be assigned to a preliminary health care cohort. As the 100 encounters are reviewed, the same primary intervention code (from SNOMED, for example) may be utilized to identify the level of fusion. So if 25 of the 100 encounters had a two level fusion from L3 to L5, all the 25 encounters may be coded with the same primary intervention codes to indicate the two level fusion. Consistent data elements may mean that when additional intervention codes are added to an encounter, a standard coding system is utilized (e.g., ensured) such that two different intervention codes are not utilized to represent the same definition.

The computing device 102 may aggregate data. Some of the encounters may be assigned to a health care cohort and/or some of the encounters may need further review to understand the association of the encounter and the primary intervention. In some configurations, the computing device 102 may return to determine 1004 whether the encounter fits a health care cohort definition. For example, the computing device 102 may make the determination 1004 with updated health care cohort definition(s).

If the computing device 102 determines 1014 that the encounter does not need further clinical review, the computing device 102 may determine 1016 whether the encounter is associated with a predefined health care cohort. For example, the computing device 102 may determine whether the encounter has a primary intervention associated with a health care cohort.

If the computing device 102 determines 1016 that the encounter associated with the primary intervention is included in a predefined health care cohort, the computing device 102 may assign 1018 the encounter to a health care exhort. For example, the computing device 102 may store the encounter in a health care exhort table. A health care exhort may include one or more encounters that should have qualified for the definition of a health care cohort, but because of one or more criteria, the encounter is moved to the health care exhort. For example, the appendectomy cohort may only include encounters that had a single surgery (appendectomy) during a patient's stay. If a patient also had their gallbladder removed during their appendectomy surgery, this encounter may be included in an appendectomy health care exhort.

The computing device 102 may determine 1020 whether the encounter has data quality issues. This may be accomplished as described in connection with one or more of FIGS. 1-2, 4 and 7-9, for instance. For example, the computing device 102 may determine whether the encounter has data quality issues by applying one or more of the approaches for detecting data quality issues described herein to the encounter.

If the computing device 102 determines 1020 that the encounter does not have data quality issue(s), the computing device 102 may generate 1012 one or more reports. This may be accomplished as described in connection with one or more of FIGS. 1-2, 4, 8-9, 12 and 14, for instance. In some configurations, the one or more reports may be generated 1012 based on the health care exhort.

If the computing device 102 determines 1020 that the encounter has data quality issues, the computing device 102 may reject 1022 the encounter (because the data needs to be cleaned, for example) and/or may reject 1024 the health care exhort. For example, the computing device 102 may not utilize the encounter as valid data. The computing device 102 may produce 1026 a data issues report. For example, the computing device 102 may generate a report that indicates one or more encounters, health care cohorts, health care exhorts, and/or general billing groups with data quality issues.

If the computing device 102 determines 1016 that the encounter is not associated with the primary intervention in a predefined health care cohort, the computing device 102 may assign 1034 the encounter to a general billing group. For example, the computing device 102 may store the encounter in a general billing group table.

The computing device 102 may determine 1036 whether the encounter has data quality issues. This may be accomplished as described in connection with one or more of FIGS. 1-2, 4 and 7-9, for instance. For example, the computing device 102 may determine whether the encounter has data quality issues by applying one or more of the approaches for detecting data quality issues described herein to the encounter.

If the computing device 102 determines 1036 that the encounter does not have data quality issue(s), the computing device 102 may generate 1012 one or more reports. This may be accomplished as described in connection with one or more of FIGS. 1-2, 4, 8-9, 12 and 14, for instance. In some configurations, the one or more reports may be generated 1012 based on the based on the general billing group.

If the computing device 102 determines 1036 that the encounter has data quality issues, the computing device 102 may reject 1038 the encounter (because the data needs to be cleaned, for example) and/or may reject 1040 the general billing group. For example, the computing device 102 may not utilize the encounter as valid data. The computing device 102 may produce 1026 a data issues report. For example, the computing device 102 may generate a report that indicates one or more encounters, health care cohorts, health care exhorts, and/or general billing groups with data quality issues.

Figure 11:
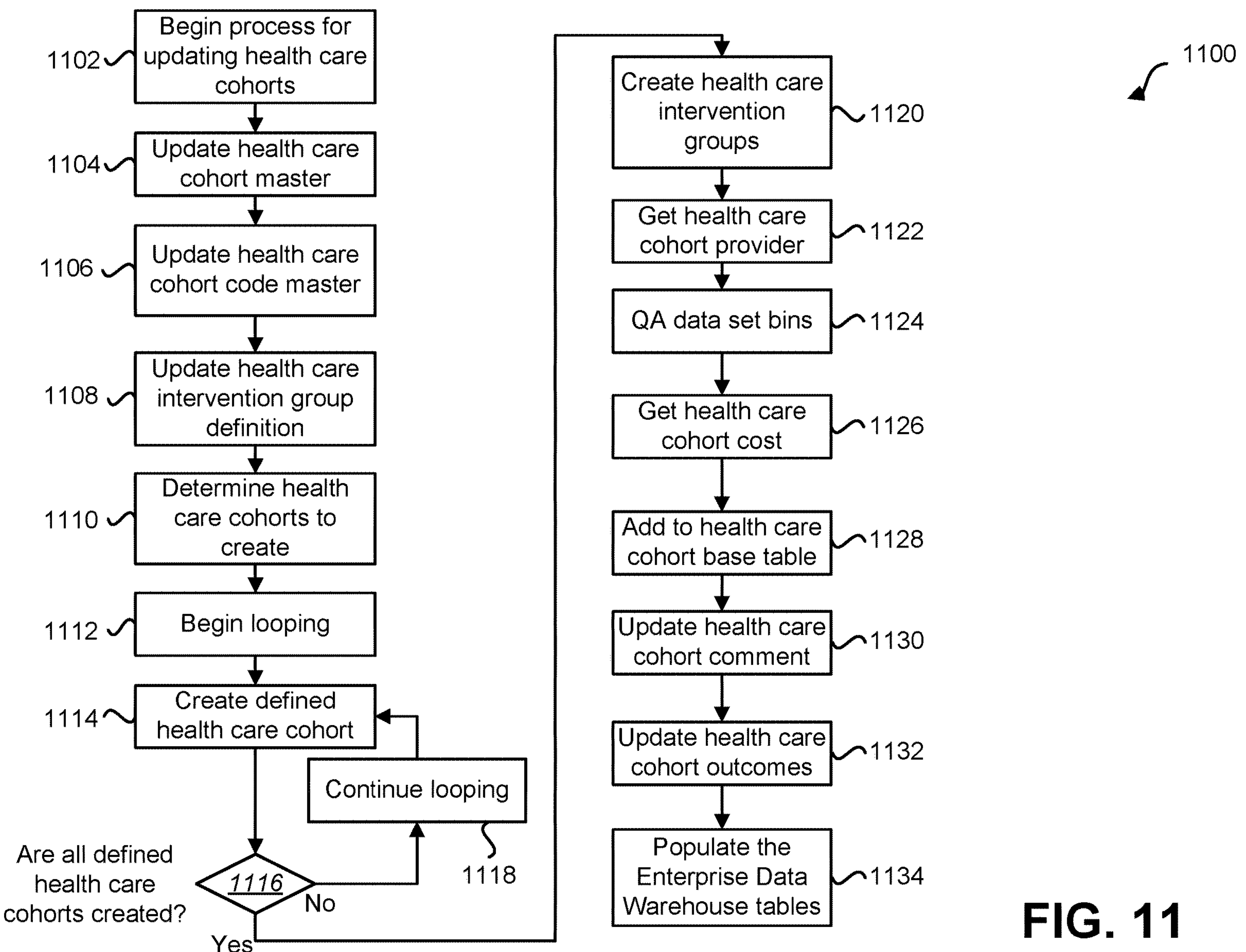
FIG. 11 is a flow diagram illustrating a method for populating one or more database tables.

FIG. 11 is a flow diagram illustrating a method 1100 for populating one or more database (e.g., EDW) tables. For example, the method 1100 may include running a diagnostic process for health care cohorts referred to as Extract, Transform, Load (ETL). The method 1100 may be performed by the computing device 102 described in connection with FIG. 1. The method 1100 may be a more specific example of populating 414 the health care cohort table(s) as described in connection with FIG. 4.

The computing device 102 may begin 1102 the process for updating health care cohorts. For example, the computing device 102 may initiate the update process and/or may receive an input indicating a command to initiate the update process.

The computing device 102 may update 1104 the health care cohort master table to include new or recently activated defined health care cohorts. For example, the computing device 102 may add one or more new and/or recently activated defined health care cohorts to a health care cohort master table. For example, one or more defined health care cohorts may have been defined and/or approved for inclusion in the health care cohorts report.

The computing device 102 may update 1106 the health care cohort code master table. For example, the computing device 102 may update 1106 the health care cohort code master table with codes of the most recent health care cohort definition. Definitions of health care intervention groups may be recreated by using codes found in the health care cohort code master. Only codes that are not in the health care cohort code master may be used for health care intervention groups in some configurations. A health care intervention group may be based on encounters that use codes that are not included in any defined health care cohort definition.

The computing device 102 may determine 1110 health care cohorts to create. For example, the computing device 102 may determine which of the health care cohorts in the health care cohort master table are not already created (e.g., may determine a list of health care cohorts to create).

The computing device 102 may begin 1112 looping in which health care cohorts are created. For example, the computing device 102 may start looping through the list of health care cohorts to create. The loop may include creating 1114 a defined health care cohort, determining 1116 if all defined health care cohorts are created and continuing 1118 to loop if all of the defined health care cohorts are not created. For example, the computing device 102 may create 1114 a defined health care cohort based on the definition in the health care cohort code master table. Each health care cohort may include additional data (e.g., costs, clinical notes, other data, etc.) for each health care cohort encounter. The loop continues 1118 to be repeated until a defined health care cohort is created.

If the computing device 102 determines 1116 that there are no more health care cohorts to be created, the computing device 102 may create 1120 one or more health care intervention groups. For example, health care intervention groups are created 1120 based on the definition determined. All health care cohorts, including defined and undefined may be complete at this point in some configurations.

The computing device 102 may get 1122 one or more health care provider(s) for each encounter. For example, the computing device 102 may determine the attending provider (s) for each encounter.

The computing device 102 may create 1124 one or more quality assurance (QA) data set bins. For example, the computing device 102 may create QA data for specific health care cohorts, which isolates encounters with data quality issues. If the quality issues are found, the computing device 102 (e.g., ETL process) may reject the encounter and assign a bin number. The rejected encounters may be added to a health care cohort QA bin table.

The computing device 102 may get 1126 one or more health care cohort cost(s). For example, the computing device 102 (e.g., ETL process) may determine the total cost for each encounter. Data (e.g., provider, QA data set bin(s) and/or cost) may be added 1128 to the health care cohort base table.

The computing device 102 may update 1130 health care cohort comments. For example, the computing device 102 may receive, associate and/or add one or more comments (e.g., user comments) to the health care cohort.

The computing device 102 may update 1132 health care cohort outcomes. For example, the computing device 102 may associate (e.g., add, store, etc.) outcomes for each encounter. In some configurations, the ETL process may be complete at this point.

Using data update in accordance with above described steps, the computing device 102 may populate 1134 the database (e.g., EDW) tables. In some configurations, results may be output to the EDW tables for data review. In some situations, populating 1134 the database (e.g., EDW) tables may be initiated based on a received input and/or through computational queries and/or ETL procedures.

Figure 12:
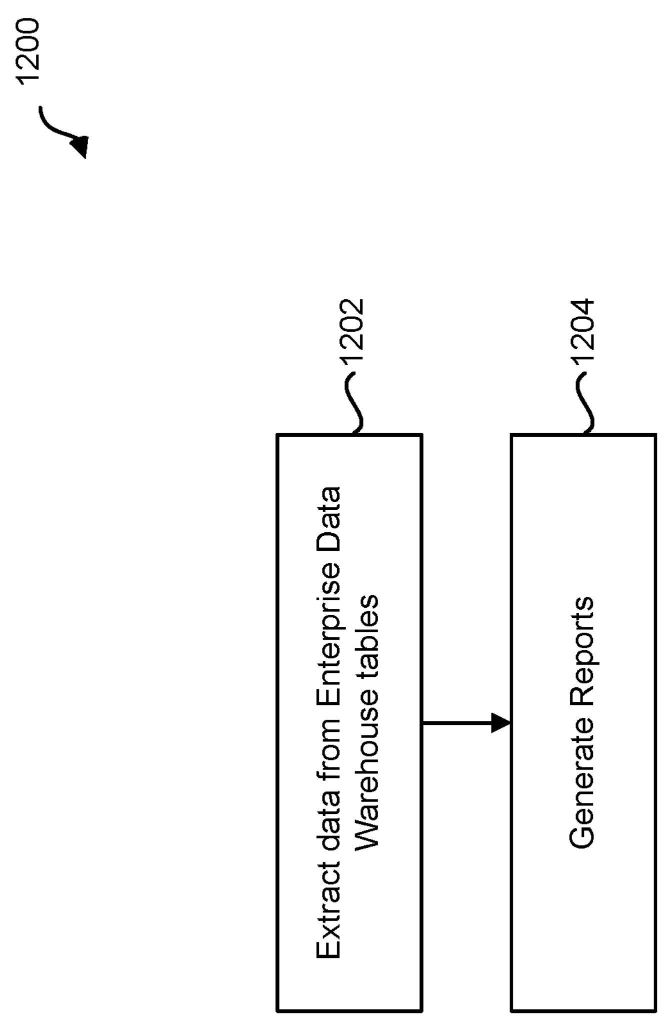
FIG. 12 is a flow diagram illustrating one configuration of a method for generating one or more reports based on data from database tables.

FIG. 12 is a flow diagram illustrating one configuration of a method 1200 for generating one or more reports based on data from database (e.g., EDW) tables. The method 1200 may include generating analytic reports using health care cohort data extracted from EDW tables, for example. The method 1200 may be performed by the computing device 102 and/or electronic device(s) 110 described in connection with FIG. 1. The computing device 102 may extract 1202 data from database (e.g., EDW) tables. For example, the computing device 102 may request (e.g., query) and/or receive health care cohort data from one or more database (e.g., EDW) tables. The database(s) may be stored on the computing device 102 and/or on one or more electronic devices 110.

The computing device 102 may generate 1204 reports. For example, the computing device may generate one or more report metrics based on the extracted data. Additionally or alternatively, the computing device 102 may load one or more report metrics into a report format (e.g., report tables, graphs, etc.). Additionally or alternatively, the computing device 102 may render the report(s) for display based on the extracted data (e.g., extracted health care cohort data, metrics based on the extracted data, etc.). In some configurations, generating 1204 report(s) may be accomplished in accordance with the description in connection with one or more of FIGS. 1-2, 4, 8-10 and 14.

Figure 13:
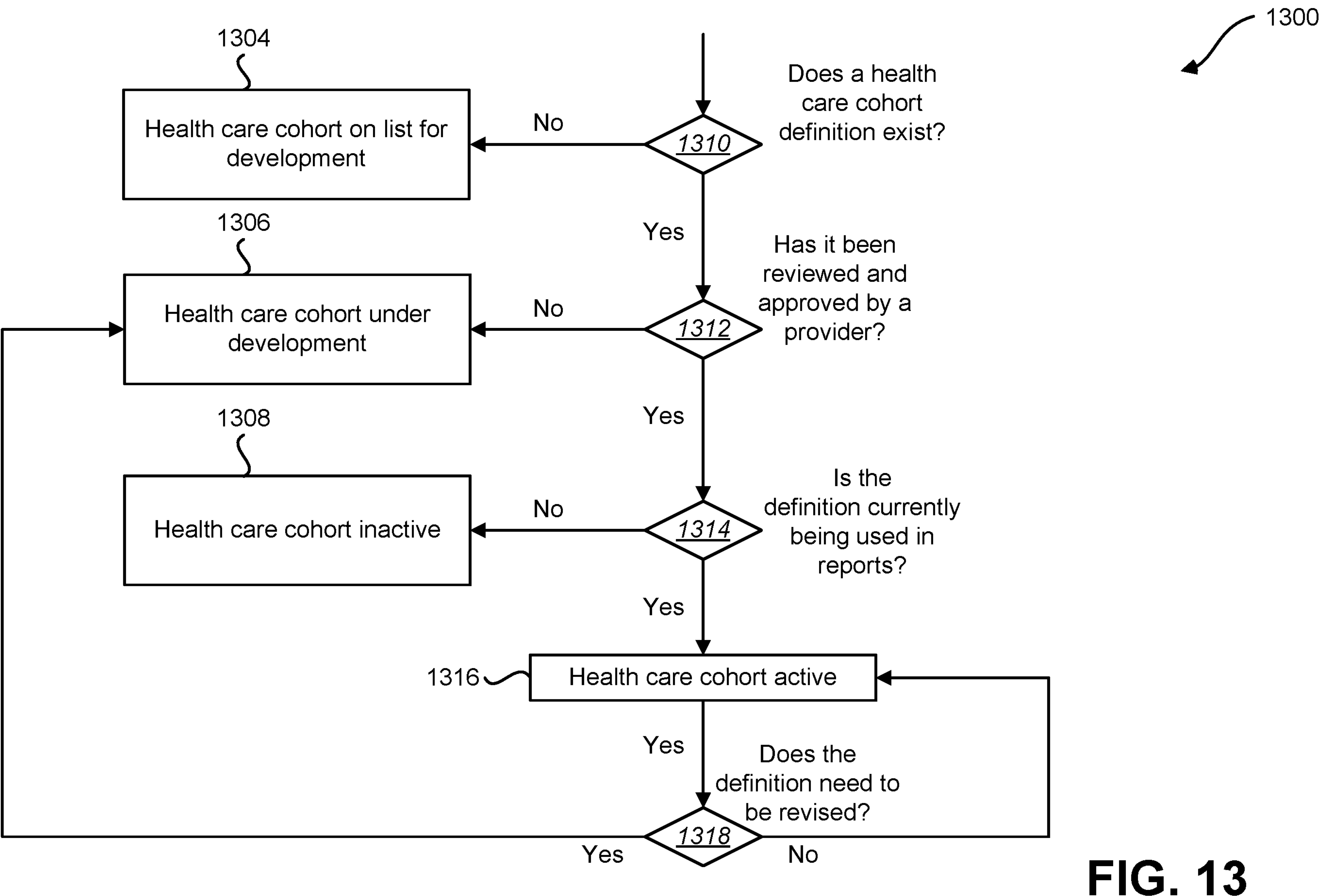
FIG. 13 is a flow diagram illustrating a method for defining a health care cohort status.

FIG. 13 is a flow diagram illustrating a method 1300 for assigning a health care cohort status. The method 1300 may be performed by the computing device 102 in connection with FIG. 1.

The computing device 102 may determine 1310 whether a definition exists for a health care cohort. For example, the computing device 102 may determine whether a health care cohort table in a database (e.g., EDW) includes a definition. If the computing device 102 determines 1310 that no definition exists for a health care cohort, the computing device 102 may add 1304 the health care cohort (e.g., a health care cohort identifier) to a list for development. For example, the computing device 102 may assign a development status for the health care cohort.

If the computing device 102 determines 1310 that a definition exists for a health care cohort, the computing device 102 may determine 1312 whether the health care cohort definition has been reviewed and approved (by a health care provider, for example). For example, the computing device 102 may determine whether an approval (and/or an indication of review) has been received for the health care cohort. If the computing device 102 determines 1312 that a health care cohort has not been approved (e.g., reviewed and approved) by a provider, the computing device 102 may assign 1306 an “under development” status for the health care cohort. For example, the computing device 102 may add the health care cohort (e.g., a health care cohort identifier) to a list indicating that the health care cohort is under development. A health care cohort may be under development during the data review to identify what encounter data will and will not be included in the health care cohort definition. Development may include reviewing the intervention code types (e.g., mandatory code types, allowable code types and/or exclusionary code types). Examples of intervention code types are described in connection with FIG. 6.

If the computing device 102 determines 1312 that a health care cohort definition has been reviewed and approved by a provider, the computing device 102 may determine 1314 whether the health care cohort definition is currently being used in reports (e.g., analytic reports). For example, the computing device may determine whether the health care cohort is set to be utilized in reports (as indicated by a parameter associated with the health care cohort, for example).

If the computing device 102 determines 1314 that the health care cohort definition is not currently being used in reports, the computing device 102 may assign 1308 an “inactive” status for the health care cohort. For example, the computing device 102 may add the health care cohort (e.g., a health care cohort identifier) to a list indicating that the health care cohort is inactive. If a health care cohort is inactive, it may not be used to populate the health care cohort tables in the EDW.

If the computing device 102 determines 1314 that the health care cohort definition is currently being used in reports, the computing device 102 may assign 1316 an “active” status for the health care cohort. For example, the computing device 102 may add the health care cohort (e.g., a health care cohort identifier) to a list indicating that the health care cohort is active.

The computing device 102 may determine 1318 whether the health care cohort definition needs to be revised. For example, reasons for a health care cohort revision may include intervention evolution, emergence of new health care supplies and equipment or techniques and/or if an indication to refine the existing health care cohort definition is received. If the health care cohort needs to be revised, the health care cohort status may be assigned 1306 as “under development.” If the health care cohort does not need to be revised, the health care cohort may remain active.

Figure 14:
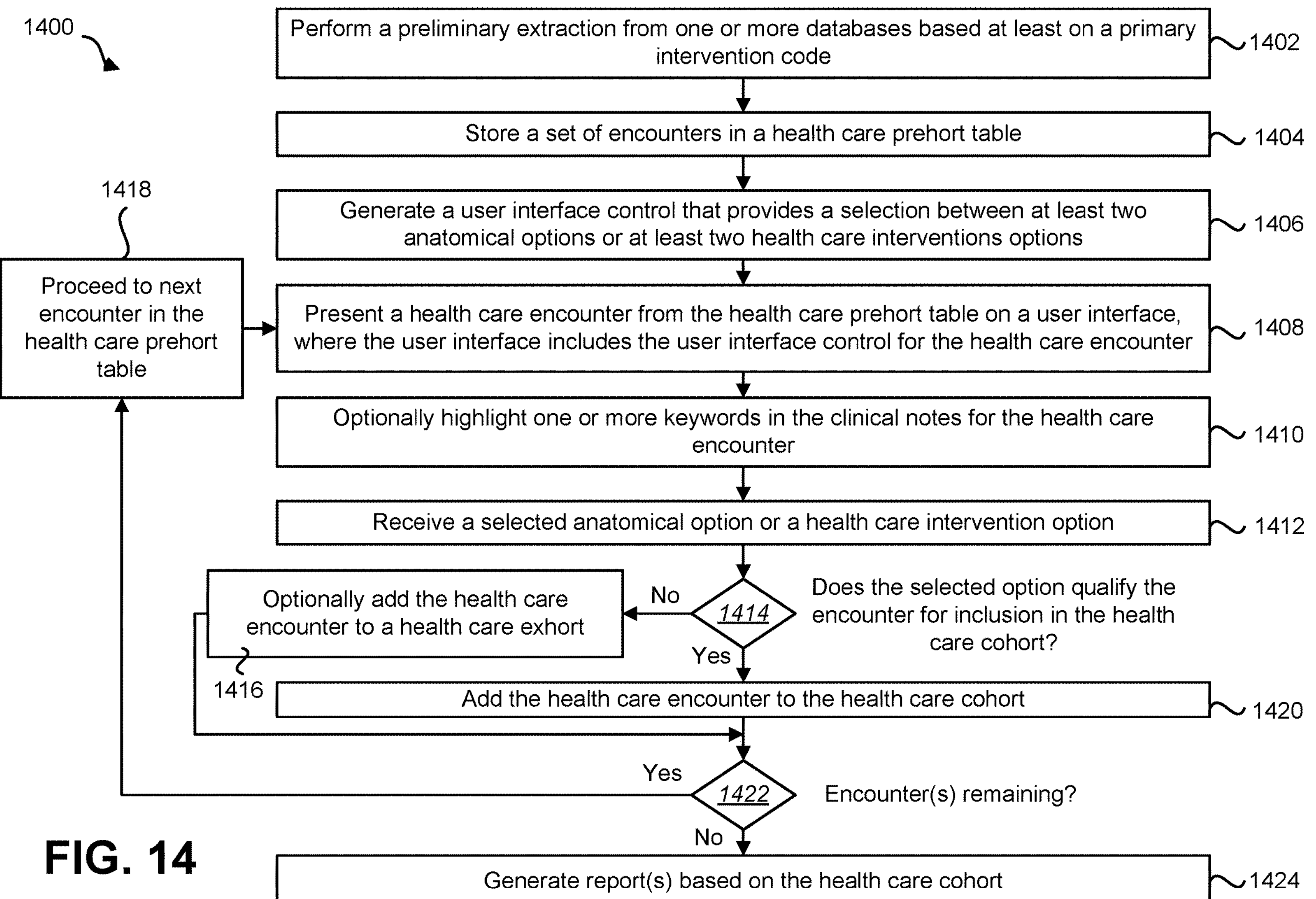
FIG. 14 is a flow diagram illustrating a method 1400 for refining a preliminary cohort.

FIG. 14 is a flow diagram illustrating a method 1400 for refining a preliminary health care cohort (health care prehort). The method 1400 may be performed by the computing device 102 described in connection with FIG. 1. For example, the cohort creator 118 described in connection with FIG. 1 may include a health care prehort refiner (e.g., cohort extractor) in some configurations. The health care prehort refiner may perform one or more of the operations of the method 1400.

The computing device 102 may perform 1402 a preliminary extraction from one or more databases based at least on a primary intervention code. This may be accomplished as described in connection with one or more of FIGS. 1 and 4-5. For example, the computing device 102 may extract (e.g., request, query, retrieve, etc.) one or more encounters with a primary intervention code (e.g., ICD code, CPT code, etc.) from one or more databases (e.g., an EDW).

The computing device 102 may store 1404 a set of encounters in a health care prehort table. For example, the computing device 102 may store 1404 the encounters extracted from the database(s) with a primary intervention code in a health care prehort table. In some configurations, the health care prehort table may be stored in one or more databases (e.g., an EDW). For example, the health care prehort table may be stored on the computing device 102 and/or on one or more electronic devices 110.

The computing device 102 may generate 1406 a user interface control that provides a selection between at least two anatomical options or at least two health care intervention options. For example, the computing device 102 may generate one or more controls (e.g., check box(es), drop-down list(s), radio button(s), button(s), selectable pane(s), selectable text(s), selectable list(s), etc.) on a user interface (e.g., user interface 114) that provide a selection between two or more anatomical options (e.g., spine levels such as L1, L2 or L3, etc.) or two or more health care intervention options (e.g., abdominal hysterectomy, a laparoscopic hysterectomy, a robotic laparoscopic hysterectomy, etc.). The selection may indicate a classification between different types (e.g., cohorts) of health care interventions. In some configurations, the computing device 102 may generate 1406 one or more user interface controls for anatomical options and health care intervention options.

The computing device 102 may present 1408 an encounter from the health care prehort table on a user interface, where the user interface includes the user interface control for the encounter. For example, the computing device 102 may present data corresponding to an encounter on the user interface. In some configurations, the user interface may include the user interface control for the selection (on one area or pane of the user interface, for example) and data (e.g., clinical notes) from the encounter (on another area or pane of the user interface, for example). For instance, the computing device 102 may present clinical notes from an encounter on the user interface.

The computing device 102 may optionally highlight 1410 one or more keywords in the clinical notes for the encounter. For example, the computing device 102 may search the clinical notes for one or more keywords (e.g., “L1,” “L2,” “L3,” “laparoscopic,” etc.). The computing device 102 may highlight (e.g., emphasize, underline, bold, color, circle, present an icon next to, etc.) the keywords. In some configurations, the computing device 102 may present (e.g., scroll the clinical notes to) a portion of the clinical notes with a high concentration (e.g., density) of keywords and/or relevant information. Additionally or alternatively, the computing device 102 may zoom in on a portion of the clinical notes with a high concentration (e.g., density) of keywords. In some configurations, the computing device 102 may provide a skip feature that enables jumping from one keyword in the clinical notes to a next keyword based on an input (e.g., mouse click, keyboard key input (e.g., down arrow, “n” for next, etc.)). The highlighting (and/or one or more other features such as scrolling, zooming, skipping, etc.) may enable a user to more quickly find information that is relevant to the type (e.g., classification, health care cohort, etc.) of an encounter.

The computing device 102 may receive 1412 a selected anatomical option or a health care intervention option. For example, the computing device 102 may receive an input (e.g., mouse click, keyboard input, touch input, pointer input, a network message, etc.) that indicates a selected anatomical option or a health care intervention option. For instance, the input may indicate a number of levels for a spinal fusion, a type of hysterectomy, etc. In some configurations, the computing device 102 may receive multiple inputs for multiple options (e.g., multiple anatomical options, multiple health care intervention options, both an anatomical option and a health care intervention option, one or more of both, etc.).

The computing device 102 may determine 1414 whether the selected option qualifies the encounter for inclusion in the health care cohort. For example, the computing device 102 may determine 1414 whether the selected anatomical option(s) and/or selected health care intervention option(s) fit the definition of the health care cohort. For instance, if an encounter is a laparoscopic hysterectomy that is consistent with a laparoscopic hysterectomy cohort, the computing device 102 may determine 1414 that the encounter is qualified for inclusion in the health care cohort. However, for instance, if an encounter is an abdominal hysterectomy that is inconsistent with the laparoscopic hysterectomy cohort, the computing device 102 may determine 1414 that the encounter is not qualified for inclusion in the health care cohort.

If the computing device 102 determines 1414 that the selected option qualifies the encounter for inclusion in the health care cohort, the computing device 102 may add 1420 the encounter to the health care cohort. For example, the electronic device may store the encounter in the health care cohort table in a database (e.g., EDW).

If the computing device 102 determines 1414 that the selected option does not qualify the encounter for inclusion in the health care cohort, the computing device 102 may optionally add 1416 the encounter to a health care exhort. For example, the computing device 102 may store the encounter in a health care exhort table in a database (e.g., EDW). A health care exhort may be a health care cohort with one or more encounters that are excluded from another health care cohort. For example, a health care exhort may be a health care cohort which includes one or more encounters that have a primary intervention code that is the same that of another health care cohort, but that have one or more excluding factors (e.g., exclusionary secondary interventions, one or more other parameters that are inconsistent with another health care cohort, etc.).

The computing device 102 may determine 1422 whether there are encounters remaining to refine. For example, the computing device 102 may determine whether there are any encounters remaining in the health care prehort table. If one or more encounters remain, the computing device 102 may proceed 1418 to a next encounter in the health care prehort table. The computing device 102 may repeat one or more steps of the method 1400 for each remaining encounter. For example, the computing device 102 may present 1408 the next encounter from the health care prehort table on the user interface, as described above.

If the computing device 102 determines 1422 that there are no encounters remaining, the computing device 102 may generate 1424 one or more reports based on the health care cohort. This may be accomplished as described in connection with one or more of FIGS. 1-2, 4, 8-10 and 12.

In some configurations, the method 1400 may be implemented to reduce and/or minimize an amount of time and/or input for classifying encounters. For example, the computing device 102 may present encounters from the health care prehort table in a serial fashion (e.g., one after another, one at a time, etc.) in order to allow a user (e.g., health care provider, nurse, etc.) to quickly review a number of encounters and provide input for classifying an encounter. In some configurations, the method 1400 may classify an encounter based on a single input (e.g., click). Additionally or alternatively, the method 1400 may automatically proceed 1418 to a next encounter after the single input. Accordingly, the method 1400 may ameliorate the burden of requiring a user to manually look up a set of encounters and/or manually search for information relevant to the classification (e.g., health care cohort) for an encounter. It should be noted that the method 1400 may be performed in conjunction with one or more other methods 200, 400, 500, 600, 700, 800, 900, 1000, 1100, 1200, 1300 described herein and/or in conjunction with one or more steps of one or more other methods 200, 400, 500, 600, 700, 800, 900, 1000, 1100, 1200, 1300 described herein.

Figure 15:
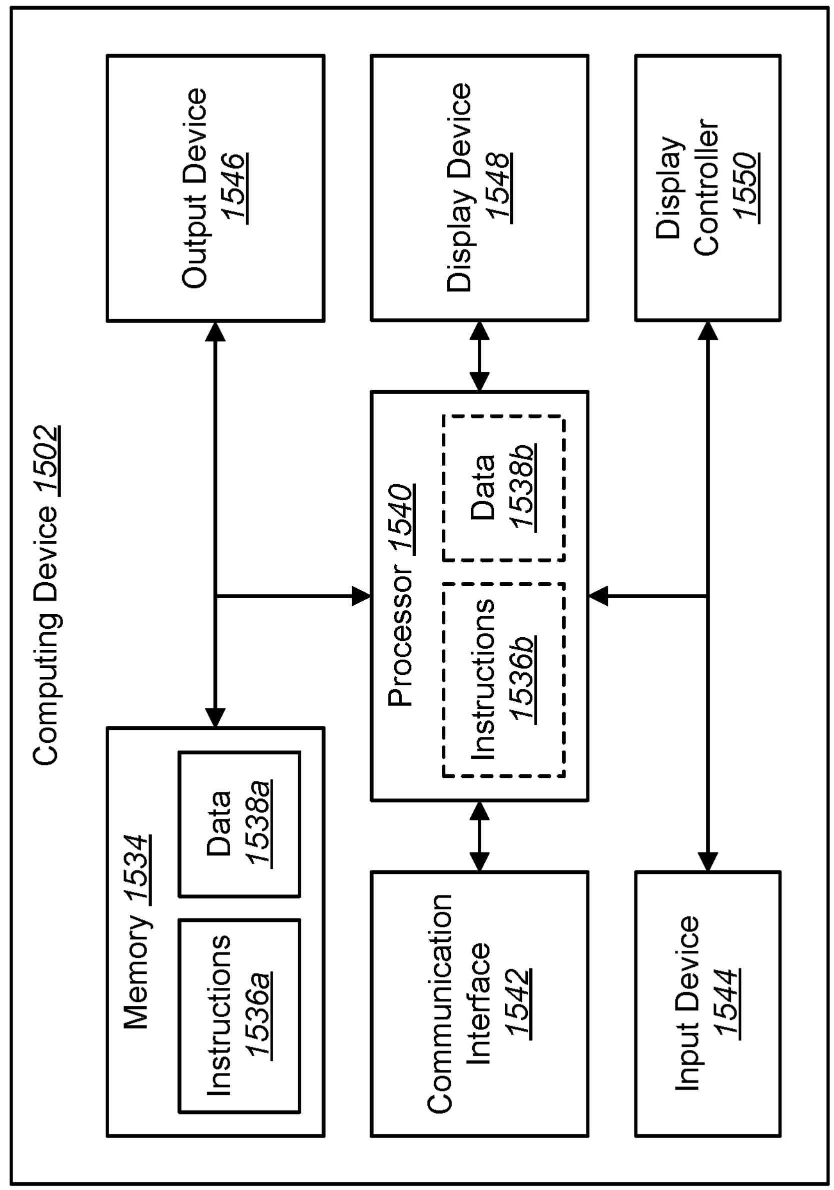
FIG. 15 illustrates various components of a computing device that may be implemented in accordance with one or more of the systems and methods disclosed herein.

FIG. 15 illustrates various components of a computing device 1502 that may be implemented in accordance with one or more of the systems and methods disclosed herein. The illustrated components may be located within the same physical structure or in separate housings or structures.

The computing device 1502 may include a processor 1540 and memory 1534. The processor 1540 controls the operation of the computing device 1502 and may be implemented as a microprocessor, a microcontroller, a digital signal processor (DSP) or other device known in the art. The memory 1534 may include instructions 1536*a* and data 1538*a*. The processor 1540 typically performs logical and arithmetic operations based on program instructions 1536*a* and data 1538*a* stored within the memory 1534. For example, instructions 1536*b* and/or data 1538*b* may be stored and/or run on the processor 1540.

The computing device 1502 typically may include one or more communication interfaces 1542 for communicating with other electronic devices. The communication interfaces 1542 may be based on wired communication technology, wireless communication technology, or both. Examples of different types of communication interfaces 1542 include a serial port, a parallel port, a Universal Serial Bus (USB), an Ethernet adapter, an IEEE 1394 bus interface, a small computer system interface (SCSI) bus interface, an infrared (IR) communication port, a Bluetooth wireless communication adapter, and so forth.

The computing device 1502 typically may include one or more input devices 1544 and/or one or more output devices 1546. As stated above, examples of different kinds of input devices 1544 include a keyboard, mouse, microphone, remote control device, button, joystick, trackball, touchpad, lightpen, etc. Examples of different kinds of output devices 1546 include a speaker, printer, etc.

One specific type of output device that may be typically included in a computer system is a display device 1548. Display devices 1548 used with configurations disclosed herein may utilize any suitable image projection technology, such as liquid crystal display (LCD), light-emitting diode (LED), gas plasma, electroluminescence, a cathode ray tube (CRT), or the like. A display controller 1550 may also be provided for converting data 1538*a* stored in the memory 1534 into text, graphics, and/or moving images (as appropriate) shown on the display device 1548.

Many features of the configurations disclosed herein may be implemented as computer software, electronic hardware, or combinations of both. To clearly illustrate this interchangeability of hardware and software, various components will be described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present systems and methods.

Where the described functionality is implemented as computer software, such software may include any type of computer instruction or computer executable code located within a memory device and/or transmitted as electronic signals over a system bus or network. Software that implements the functionality associated with components described herein may include a single instruction, or many instructions, and may be distributed over several different code segments, among different programs, and across several memory devices.

The term "determining" (and grammatical variants thereof) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

Information and signals may be represented using any of a variety of different technologies and techniques. For example, data, instructions, commands, information, signals, bits, symbols and chips that may be referenced throughout the above description may be represented by voltages, currents, electromagnetic waves, magnetic fields or particles, optical fields or particles, or any combination thereof.

The various illustrative logical blocks and modules described in connection with the configurations disclosed herein may be implemented or performed with a general purpose processor, a digital signal processor (DSP), an application specific integrated circuit (ASIC), a field programmable gate array signal (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the configurations disclosed herein may be configured directly in hardware, in a software module executed by a processor, or in a combination of the two. A software module may reside in random-access memory (RAM) memory, flash memory, read-only memory (ROM) memory, erasable programmable ROM (EPROM) memory, electrically EPROM (EEPROM) memory, registers, hard disk, a removable disk, a compact disc ROM (CD-ROM) or any other form of storage medium known in the art (e.g., such as a non-transitory computer-readable). An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The methods disclosed herein include one or more steps or actions for achieving the described method. The method steps and/or actions may be interchanged with one another without departing from the scope of the present systems and methods. In other words, unless a specific order of steps or actions is required for proper operation of the configuration, the order and/or use of specific steps and/or actions may be modified without departing from the scope of the present systems and methods.

It is to be understood that the claims are not limited to the precise configuration and components illustrated above. Various modifications, changes and variations may be made in the arrangement, operation and details of the systems, methods, and apparatus described herein without departing from the scope of the claims.

What is claimed is:

1. A method for generating a report by a computing device, comprising:

receiving an input that indicates a primary intervention code;

identifying a specific health care intervention by performing a preliminary extraction from one or more databases based on at least the primary intervention code;

storing a set of encounters for the specific health care intervention in a health care prehort table;

generating a user interface control that provides a selection between at least two anatomical options or at least two health care intervention options;

receiving a selected anatomical option or a health care intervention option;

creating a health care cohort for the specific health care intervention, wherein the health care cohort comprises a definition of a primary intervention based on the set of encounters from the health care prehort table and the selected anatomical option or health care intervention option;

performing an encounter analysis to identify one or more comparative metrics associated with the health care cohort and one or more related health care cohorts, and to determine variations of the one or more comparative metrics associated with the health care cohort and the one or more related health care cohorts, wherein the one or more comparative metrics include costs, and wherein the variations identify encounters that have exceeded a threshold proportion of costs more than one standard deviation from an average cost of the health care cohort; and generating a report based on the health care cohort, wherein the report comprises a list of cohorts and the variations between the health care cohort and the one or more related health care cohorts from the encounter analysis, wherein the report identifies the encounters that have exceeded the threshold proportion of costs more than one standard deviation from the average cost of the health care cohort, and wherein the report compares the average cost of the health care cohort by region, facility, or physician.

2. The method of claim 1, wherein the health care cohort comprises a list of associated acceptable secondary interventions.

3. The method of claim 2, wherein the health care cohort further comprises a list of exclusionary secondary interventions that if performed would exclude a corresponding encounter from the health care cohort.

4. The method of claim 1, wherein the report comprises a system-specific report.

5. The method of claim 4, wherein the system-specific report comprises a hospital-specific or site-specific report.

6. The method of claim 1, wherein the report comprises a health care provider-specific report.

7. The method of claim 1, wherein the report comprises a list of cohorts organized relative to a cost variation per encounter compared to an average.

8. The method of claim 1, further comprising cleaning health care cohort data.

9. An apparatus for generating a report, the apparatus comprising:

a processor;

memory in electronic communication with the processor; and instructions stored in the memory, the instructions being executable to:

receive an input that indicates a primary intervention code;

identify a specific health care intervention by performing a preliminary extraction from one or more databases based on at least the primary intervention code;

store a set of encounters for the specific health care intervention in a health care prehort table;

generate a user interface control that provides a selection between at least two anatomical options or at least two health care intervention options;

receive a selected anatomical option or a health care intervention option;

create a health care cohort for the specific health care intervention, wherein the health care cohort comprises a definition of a primary intervention based on the set of encounters from the health care prehort table and the selected anatomical option or health care intervention option;

perform an encounter analysis to identify one or more comparative metrics associated with the health care cohort and one or more related health care cohorts, and determine variations of the one or more comparative metrics associated with the health care cohort and the one or more related health care cohorts, wherein the one or more comparative metrics include costs, and wherein the variations identify encounters that have exceeded a threshold proportion of costs more than one standard deviation from an average cost of the health care cohort; and generate a report based on the health care cohort, wherein the report comprises a list of cohorts and the variations between the health care cohort and the one or more related health care cohorts from the encounter analysis, wherein the report identifies the encounters that have exceeded the threshold proportion of costs more than one standard deviation from the average cost of the health care cohort, and wherein the report compares the average cost of the health care cohort by region, facility, or physician.

10. The apparatus of claim 9, wherein the health care cohort comprises a list of associated acceptable secondary interventions.

11. The apparatus of claim 10, wherein the health care cohort further comprises a list of exclusionary secondary interventions that if performed would exclude a corresponding encounter from the health care cohort.

12. The apparatus of claim 9, wherein the report comprises a system-specific report.

13. The apparatus of claim 12, wherein the system-specific report comprises a hospital-specific or site-specific report.

14. The apparatus of claim 9, wherein the report comprises a health care provider-specific report.

15. The apparatus of claim 9, wherein the report comprises a list of cohorts organized relative to a cost variation per encounter compared to an average.

16. The apparatus of claim 9, wherein the instructions are further executable to clean health care cohort data.

17. A method for refining a health care prehort by a computing device, comprising:

performing a preliminary extraction from one or more databases based at least on a primary intervention code, wherein the preliminary extraction extracts clinical notes;

storing a set of encounters in a health care prehort table;

generating a user interface control that provides a selection between at least two anatomical options or at least two health care intervention options;

for each encounter in the health care prehort table:

presenting an encounter from the health care prehort table on a user interface, wherein the user interface includes the user interface control for the encounter;

receiving a selected anatomical option or a health care intervention option; and adding the encounter to a health care cohort if the selected anatomical option or health care intervention option qualifies the encounter for inclusion in the health care cohort;

performing an encounter analysis to identify one or more comparative metrics associated with the health care cohort and one or more related health care cohorts, and to determine variations of the one or more comparative metrics associated with the health care cohort and the one or more related health care cohorts;

enriching the set of encounters with the clinical notes;

identifying one or more keywords in the clinical notes that describe differences for each encounter; and generating one or more reports based on the health care cohort, wherein the report comprises a list of cohorts and the variations between the health care cohort and the one or more related health care cohorts from the encounter analysis, and wherein the report further comprises at least a portion of the clinical notes with the one or more keywords emphasized.

18. The method of claim 17, further comprising highlighting the one or more keywords in clinical notes for the encounter.

19. An apparatus for refining a health care prehort, the apparatus comprising:

a processor;

memory in electronic communication with the processor; and instructions stored in the memory, the instructions being executable to:

perform a preliminary extraction from one or more databases based at least on a primary intervention code, wherein the preliminary extraction extracts clinical notes;

store a set of encounters in a health care prehort table;

generate a user interface control that provides a selection between at least two anatomical options or at least two health care intervention options;

for each encounter in the health care prehort table:

present an encounter from the health care prehort table on a user interface, wherein the user interface includes the user interface control for the encounter;

receive a selected anatomical option or a health care intervention option; and add the encounter to a health care cohort if the selected anatomical option or health care intervention option qualifies the encounter for inclusion in the health care cohort;

perform an encounter analysis to identify one or more comparative metrics associated with the health care cohort and one or more related health care cohorts, and determine variations of the one or more comparative metrics associated with the health care cohort and the one or more related health care cohorts;

enrich the set of encounters with the clinical notes;

identify one or more keywords in the clinical notes that describe differences for each encounter; and generate one or more reports based on the health care cohort, wherein the report comprises a list of cohorts and the variations between the health care cohort and the one or more related health care cohorts from the encounter analysis, and wherein the report further comprises at least a portion of the clinical notes with the keywords emphasized.

20. The apparatus of claim 19, wherein the instructions are further executable to highlight one or more keywords in clinical notes for the encounter.

* * * * *